(12) United States Patent
Ootake et al.

(10) Patent No.: US 6,451,392 B1
(45) Date of Patent: Sep. 17, 2002

(54) CHEMICAL ADSORBATE COMPOUND, ORGANIC FILM, LIQUID CRYSTAL ALIGNMENT FILM, AND LIQUID CRYSTAL DISPLAY DEVICE UTILIZING THE CHEMICAL ADSORBATE COMPOUND

(75) Inventors: Tadashi Ootake, Neyagawa; Kazufumi Ogawa, Nara; Takaiki Nomura; Takako Takebe, both of Katano, all of (JP)

(73) Assignee: Matsushita Electric Industrial Co., Ltd. (JP)

( * ) Notice: Subject to any disclaimer, the term of this patent is extended or adjusted under 35 U.S.C. 154(b) by 86 days.

(21) Appl. No.: 09/610,292

(22) Filed: Jul. 5, 2000

(30) Foreign Application Priority Data

| Jul. 5, 1999 | (JP) | 11-190001 |
| Jul. 5, 1999 | (JP) | 11-190043 |
| Aug. 26, 1999 | (JP) | 11-239727 |
| Aug. 26, 1999 | (JP) | 11-239735 |

(51) Int. Cl.$^7$ .............. C09K 19/56; C09K 19/40; C07F 7/12; G02F 1/1337; C08T 7/04
(52) U.S. Cl. .............. 428/1.23; 252/299.4; 427/387; 427/510; 427/515
(58) Field of Search .............. 427/387, 510, 427/515; 428/1.23; 252/299.4

(56) References Cited

U.S. PATENT DOCUMENTS

| 5,468,519 A | * 11/1995 | Akiyama et al. ............ 427/532 |
| 5,578,531 A | * 11/1996 | Shashidhar et al. ......... 428/1.23 |
| 5,824,377 A | * 10/1998 | Pirwitz et al. .............. 428/1.23 |
| 6,013,331 A | * 1/2000 | Ogawa ........................ 427/515 |
| 6,054,190 A | * 4/2000 | Ogawa et al. ............... 427/510 |

FOREIGN PATENT DOCUMENTS

| EP | 0 962 460 A1 | 12/1999 |
| JP | 03-7913 | 1/1991 |
| JP | 05-53118 | 3/1993 |
| JP | 05-173135 | 7/1993 |
| JP | 07-72483 | 3/1995 |
| JP | 07-318942 | 12/1995 |
| JP | 11-49781 | 2/1999 |
| JP | 11-125822 | 5/1999 |
| JP | 2000-56309 | * 2/2000 |
| WO | WO99/06415 | 2/1999 |

\* cited by examiner

*Primary Examiner*—Shean C. Wu
(74) *Attorney, Agent, or Firm*—Parkhurst & Wendel, L.L.P

(57) ABSTRACT

A novel chemical adsorbate compound capable of forming a monomolecular thin film is provided. The chemical adsorbate compound is transparent and stable in the visible light range, and has a photosensitive group which causes a photochemical reaction in the ultraviolet light range. Utilizing the chemical adsorbate compound, a liquid crystal alignment film is also provided. The liquid crystal alignment film has an excellent thermal stability and alignment control performance. Utilizing liquid crystal alignment film, a liquid crystal display device is further provided. The liquid crystal display device achieves wide viewing angles and clear display images at small driving voltages. These are achieved by, as one example, providing a chemical adsorbate compound including a chalcone derivative having a COO group at the 4' position in the chalcone skeleton and an —SiX$_3$ group, where X is a halogen, at the molecular end adjacent to the COO group. Another example of the chemical adsorbate compound is a compound in which a linear hydrocarbon group is ether-linked at the 4 position of the benzene ring in the chalcone skeleton and an —SiX$_3$ group, where X is a halogen, is ether-linked to the hydrocarbon group.

83 Claims, 12 Drawing Sheets

CHEMICAL ADSORBATE COMPOUND, ORGANIC FILM, LIQUID CRYSTAL ALIGNMENT FILM, AND LIQUID CRYSTAL DISPLAY DEVICE UTILIZING THE CHEMICAL ADSORBATE COMPOUND

BACKGROUND OF THE INVENTION

(1) Field of the Invention

The present invention relates to a novel chemical adsorbate compound chemically adsorbed onto a surface of a substrate material. This chemical adsorbate compound is usable as a functional film for modifying properties of the surface of the substrate material, and as a liquid crystal alignment film for controlling the alignment of liquid crystal molecules. The present invention also relates to a liquid crystal alignment film employing this novel chemical adsorbate compound. The present invention further relates to a liquid crystal display device comprising this liquid crystal alignment film as a component thereof.

(2) Description of the Prior Art

In recent years, as the size and weight reduction of information processing equipment advances, liquid crystal displays have increasingly found widespread use. The liquid crystal display devices generally require liquid crystal alignment films for aligning liquid crystal molecules, but not many materials are suitable for candidate materials for the liquid crystal alignment films. As the performance of the liquid crystal devices becomes increasingly higher, there is an increasing demand for novel materials for liquid crystal alignment films which exhibit improved characteristics.

Conventionally, polymers such as polyimides and polyvinyl alcohols have been utilized for the materials for liquid crystal alignment films. However, such films made of polymers are generally large in thickness and electrically insulative, and therefore tend to cause image sticking, degradation of effective electric field, and similar undesirable effects. Moreover, such films are fixed to substrates by so-called anchoring effect, thus showing weak bonding or adhesive characteristics.

In addition, such films made of polyimides or the like have a structure such that polymer molecules are bonded each other in an intricately intertwined manner, and liquid crystal molecules cannot enter inside the films. Therefore, in such films, only the surface layer where the foremost ends of the polymer molecules protrude serves to control the alignment of liquid crystal molecules, and the rest of the portion of the film does not influence the alignment of liquid crystal molecules. Hence, the films made of polymers cannot exhibit sufficient alignment control performance over liquid crystal molecules.

Furthermore, while the films made of polymers are generally given alignment control characteristic by rubbing, alignment system made by rubbing is susceptible to external degrading factors such as heat or friction. Thus, the liquid crystal alignment films made by rubbing have a drawback that the films cannot exhibit sufficient alignment control characteristic or alignment stability. Further, rubbing causes the following drawbacks.

i) When a film surface has roughness, depressed portions of the film surface cannot be rubbed. The unrubbed portions cause alignment defects, which in turn cause image sticking and unevenness in displayed images.

ii) Rubbing treatment causes static charge, which damages the TFTs formed underneath the alignment film.

iii) By rubbing, dust is produced from a rubbing cloth (cotton cloth or the like) and film surface. The dust can cause unevenness in displayed images and undesirable variation in the cell gap.

In order to provide a solution to such problems of rubbing as described above, some non-contact alignment techniques have been suggested. However, none of the techniques has yet achieved completely satisfactory results. For example, Japanese Unexamined Patent Publication No. 5-53118 discloses the following technique; a layer of a photosensitive compound is formed on a substrate, and grooves having a prescribed pattern are formed in the photosensitive compound layer by light exposure and heat treatment, thus realizing an alignment control characteristic by the grooves. This technique, however, requires a large light energy for producing the grooves. Moreover, uniform grooves are difficult to form, and unevenness in displayed images tends to occur. The alignment control performance is also insufficient.

Japanese Unexamined Patent Publication No. 7-72483 discloses the following technique; alignment control characteristic in an alignment film is realized by applying a linear polarized light to a layer of a compound for forming the alignment film containing polyimide or polyimide precursor to polymerize the polyimide or polyimide precursor. However, this technique employs polyimide, which is an organic polymer, and therefore cannot solve the problem of the large film thickness, which induces an increase in liquid crystal driving voltage. Another problem is that the adhesiveness of the resultant alignment film to the substrate is not sufficient.

Japanese Unexamined Patent Publication No. 7-318942 disclose the following technique; in an alignment film, a molecular structure having an alignment control characteristic is realized by applying a light from an oblique direction to the alignment film having a polymer structure to create different bonds or decomposition in the molecular chains in the film. However, this technique also employs alignment films made of organic polymers such as polyimide, polyvinyl alcohol, polystyrene, and the like. Therefore, this technique as well cannot solve the above-described problems of large film thickness and small adhesiveness to the substrate. In addition, this technique requires that a light be applied from an oblique direction to the alignment film in order to produce a pretilt angle, and this leads to increase in manufacturing cost since an accurate light irradiation from an oblique direction calls for a high accuracy apparatus for light irradiation.

Further, twisted-nematic mode or the like liquid crystal display devices employing prior art liquid crystal alignment film have another problem of narrow viewing angles. In view of this problem, for example, Japanese Unexamined Patent Publication No. 6-173135 discloses the following technique; an alignment film comprising a plurality of micro-regions having different liquid crystal alignment directions are realized by repeating the consecutive steps in which an alignment film is rubbed in a certain direction, thereafter prescribed regions of the rubbed film are coated with a resist, and the film is rubbed in the reverse direction. However, in order to form a plurality of domains having different alignment directions by a rubbing method (contact method), it is necessary to repeat complicated steps of masking and rubbing each time corresponding to the divided domains. Accordingly, by this technique, production efficiency is degraded, and the problems of the static charge and dust produced by rubbing are further worsened.

In order to improve viewing angles, it is. possible to employ the non-contact methods as described above. However, those prior art non-contact techniques (Japanese Unexamined Patent Publication Nos. 5-53118, 7-72483, and 7-318942) have the problems of large film thickness and insufficient adhesiveness to the substrate, and therefore cannot provide satisfactory liquid crystal alignment films.

In view of these problems, the present inventors have proposed a technique for producing a novel nanosized liquid crystal alignment film in Japanese Unexamined Patent Publication No. 3-7913. In this technique, an alignment film is composed of a monomolecular layer in which a silane-based chemical adsorbate compound (also referred to as a "surfactant") is chemically adsorbed onto a substrate surface. According to this technique, an ultra thin transparent film firmly bonded to the substrate surface can be easily formed in an efficient manner. Furthermore, this technique can provide, without rubbing, a liquid crystal alignment film having a certain alignment control performance. However, in this technique, there still is room for improvement in the thermal stability and alignment control performance of the alignment film.

SUMMARY OF THE INVENTION

The present invention comprises a series of groups, namely, a first group, a second group, a third group, and a fourth group. The series of the invention is intended to provide solutions to the above-described problems and drawbacks in prior art at one time.

Accordingly, it is a first object of the present invention to provide a novel chemical adsorbate compound capable of easily producing functional films for modifying surfaces of substrate materials and liquid crystal alignment films for controlling the alignment of liquid crystal molecules. More specifically, the first object of the invention is to provide a compound such that; a) the compound is capable of forming a nanosized film by being chemically adsorbed onto a surface of a substrate material, and b) the compound is colorless and stable to a light in the visible range (400 to 700 nm wavelength range), whereas reactive to a light in the ultraviolet range (200 to 400 nm wavelength range), and thereby the molecules are crosslinked with each other by being irradiated with ultraviolet light, forming a stable film structure. The present invention also provides a method of producing such a compound in an efficient manner.

It is a second object of the invention is to realize, by using the above chemical adsorbate compound, a non-rubbed liquid crystal alignment film having an excellent alignment control performance and thermal stability.

It is a third object of the invention to realize, by employing the above liquid crystal alignment film, a liquid crystal display device capable of achieving a wide viewing angle and clear images.

Now, each group of the invention will be described below.
(1) The First Group
  i) A chemical adsorbate compound in accordance with the first group of the invention was accomplished based on the view that a chalcone skeleton is highly photosensitive. In accordance with the first group of the invention, there is provided a chemical adsorbate compound represented by the following chemical formula 101. The chalcone skeleton means a skeleton represented by the chemical formula 104.

Chemical Formula 101

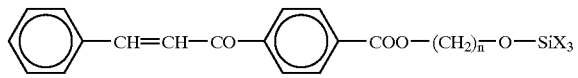

(In the formula, n is an integer from 1 to 20, and X is a halogen.)

Chemical Formula 104

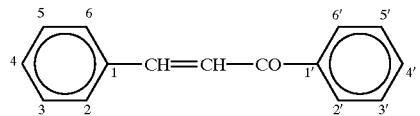

The compound shown by the chemical formula 101 has —O—$SiX_3$ group serving as a chemically adsorbed group, and therefore can be easily adsorbed onto a surface of a substrate material having hydrophilic groups (for example, OH groups, COOH groups, $NH_2$ groups, NH groups, SH groups, etc.). Thus, a monomolecular film having an extremely small thickness can be easily formed on the surface of a substrate material. The compound having a chemical structure represented by the chemical formula 101 is colorless, transparent, and chemically stable in the visible light range.

In addition, the compound of the chemical formula 101 has a carbon-carbon double bond in the molecular structure, and the ultraviolet absorption peak of the compound is in a longer wavelength range than that of conventional compounds of this type. Accordingly, by employing a light having such a wavelength, the adsorbed molecules can be crosslinked with each other without causing side reactions (decomposition). More specifically, the compound of the chemical formula 101 according to the invention has a carbonyl group at the 4' position of the benzene ring. The carbonyl group can be conjugated with the chalcone skeleton, and the conjugate length is thereby made longer than that in the case where the compound is made only of the chalcons skeleton. Therefore, the electrons in the conjugation are delocalized, and the energy level is reduced. As a result, the ultraviolet absorption wavelength is shifted to a longer wavelength range.

If the ultraviolet light employed has a short wavelength in the case where the main reaction by the light irradiation is crosslinking or polymerization, decomposition tends to occur as a side reaction. However, since the compound represented by the chemical formula 101 has the absorption peak in a longer wavelength range in the ultraviolet range, it is possible to effectively excite the carbon-carbon double bonds in the chalcone skeletons and thereby to crosslink the adsorbed molecules each other via the bonds without causing side reactions. The film made by such crosslinking has excellent water repellency and durability.

In addition, the compound represented by the chemical formula 101 has a hydrocarbon group where n=1 to 20. When n in the hydrocarbon group is in the foregoing range, the molecular length is appropriate, and therefore the compound can exhibit excellent molecular alignment characteristic and perform smooth crosslinking.

Accordingly, the compound represented by the chemical formula 101 can form an ultra thin monomolecular film firmly chemically bonded to a substrate material surface, and the resultant film shows excellent properties such as good water repellency, durability, chemical stability, and weather resistance. Hence, such a film is remarkably useful as a functional film for modifying the surface of a substrate material, and the excellent properties are particularly useful in forming a liquid crystal alignment film. The reasons why the film is suitable for a liquid crystal alignment film will now be discussed below.

As has already mentioned above, the chemical adsorbate compound of the chemical formula 101 is easily chemically bonded to the substrate material surface. Therefore, when the solution containing the chemical adsorbate compound of the chemical formula 101 contacts with the surface of the substrate as a component of a liquid crystal cell, one end of each adsorbed molecule (the end adjacent to the —O—Si bond group) is chemically bonded to the substrate while the other end protrudes in a direction far from the substrate surface. Thereby, it is made possible to form a thin film composed of an aggregate of a multiplicity of the adsorbed molecules arrayed along the substrate surface.

In such a thin film, composed of the aggregate of the adsorbed molecules, liquid crystal molecules can enter the gap spaces between the adsorbed molecules. The inclination (pretilt angle) and alignment orientation (pretilt orientation) of the liquid crystal molecules slotted in the gap spaces with respect to the substrate are restricted by the inclination and/or alignment orientation (hereinafter these are also collectively referred to as an "alignment direction") of the adsorbed molecules with respect to the substrate. Thus, by controlling the alignment direction of the adsorbed molecules, the alignment direction of the liquid crystal molecules can be arbitrarily controlled.

By employing the above-described chemical adsorbate compound, it is possible to form a film having an advantageous structure such that every individual adsorbed molecule has an influence on the alignment control of liquid crystal molecules, and the resultant film therefore exhibits a remarkably high efficiency in the alignment control performance in relation to the film thickness. In addition, the resultant film has a remarkably small thickness, leading to an excellent light transmission characteristic. Moreover, since the film is not made of polymer, the adverse effects as an electrical resistive/insulative film are small, and the film does not hinder the electric field for driving liquid crystals. Furthermore, since the adsorbed molecules in the thin film are firmly bonded to the substrate by chemical bond, the film does not easily come off from the substrate surface.

Thus, a liquid crystal alignment film capable of increasing the brightness and contrast ratio and reducing the driving voltage can be realized by employing the above-described chemical adsorbate compound. In addition, in the film employing the chemical adsorbate compound, after chemically adsorbed to the substrate, the adsorbed molecules can be crosslinked with each other at the carbon-carbon double bonds by applying an ultraviolet light to the film surface. As a result, the liquid crystal alignment characteristic of the resultant film does not degrade by external degrading factors such as heat, contacts with water or organic solvents, and so forth. Furthermore, when a polarized light is used in the ultraviolet light irradiation, crosslinking of the molecules can be caused along a specific direction. Thus, by specifying the direction of polarization, a desired alignment control characteristic can be obtained in the liquid crystal alignment film.

It is considered that crosslinking of the molecules serves to stabilize the liquid crystal alignment control characteristic since the configuration of the molecules each other becomes fixed by crosslinking of the adsorbed molecules with each other. By contrast, conventional liquid crystal alignment films (such as the above-mentioned polymer films composed of polyimides) have such a structure that long main chains are densely intertwined each other, only the surface portion of the films can contribute to the alignment control over liquid crystals, Consequently, conventional alignment films cannot achieve a sufficient alignment control performance. Moreover, if external degrading factors such as heat or friction are inflicted on conventional rubbed alignment films, the alignment control performance of the films is changed or degraded. Further, polymer films such as polyimide films are large in the film thickness and electrically insulative, and therefore degrade the effective electric field for driving liquid crystals and cause image sticking.

ii) The above-described chemical adsorbate compound may be such that n is an integer from 5 to 10, and X is chlorine in the chemical formula 101.

If n in the chemical formula 101 is less than 5, in other words, if the length of the hydrocarbon group is short, the angle or proportion of the chalcone skeleton arrayed vertically with respect to the substrate material becomes small, thereby decreasing the efficiency in the crosslinking reaction. In order for the crosslinking to progress at high efficiency, the relative positions of the carbon-carbon double bonds of the adsorbed molecules to be crosslinked are important, i.e., the photosensitive sites must be in contact with or adjacent to each other. However, when many of the molecules are arrayed horizontally with respect to the substrate, the photosensitive sites do not easily come in contact with or close to each other.

On the other hand, if n is greater than 10, the degree of freedom of molecules with respect to the substrate material surface becomes too large, which also leads to the disadvantage that the photosensitive sites do not easily come in contact with or close to each other and the efficiency of the crosslinking decreases. Accordingly, the value n is preferable to be in the range of 5 to 10.

Chloride is preferable as X in the chemical formula 101. When the X is chloride, the chemical adsorbate compound can be easily chemisorbed onto the substrate material by dehydrochlorination, and in addition, the adsorbed molecules per se can be easily synthesized.

iii) The chemical adsorbate compound in accordance with the first group of the invention can be produced by the following method comprising at least the steps of: reacting benzaldehyde and 4-acetylbenzoic acid by aldol condensation to synthesize a first chalcone derivative represented by the chemical formula 102:

Chemical Formula 102

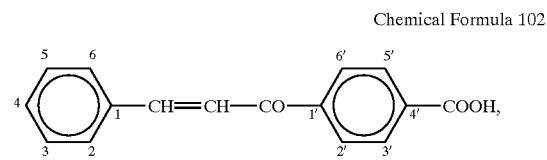

the first chalcone derivative wherein a carbonyl group is bonded at the 4' position of the benzene ring in the chalcone skeleton; and after the step of reacting benzaldehyde and 4-acetylbenzoic, reacting an alcohol derived from the first chalcone derivative with an $SiX_4$ where X is a halogen in an inert gas atmosphere by dehydrohalogenation, to synthesize a second chalcone derivative having an —O—$SiX_3$ group and a characteristic group represented by the chemical formula 103:

Chemical Formula 103

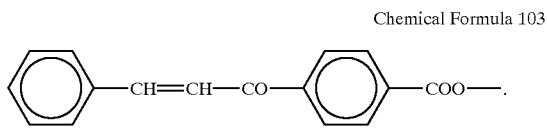

By employing this method, it is made possible to easily and efficiently produce the second chalcone derivative in which the carbonyl group is bonded at the 4' position of the benzene ring in the chalcone skeleton, and the characteristic group having the —O—$SiX_3$ group is bonded at the side of the carbonyl group. In the second chalcone derivative produced by this method, the carbon-carbon double bond (—CH=CH—) is highly sensitive to ultraviolet light, and the $SiX_3$ has high chemical adsorbing performance. In addition, since the main axis of the molecule is linear, a desirable alignment control of liquid crystal molecules is possible.

iv) The above-described method for producing a chemical adsorbate compound according to the first group of the invention may be such that the second chalcone derivative is a compound represented by the chemical formula 101:

Chemical Formula 101

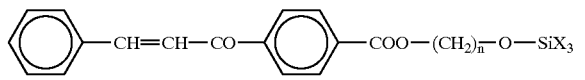

(In the formula, n is an integer from 1 to 20, and X is a halogen.)

In the chemical adsorbate compound composed of the compound represented by the chemical formula 101, the carbon-carbon double bond in the chalcone skeleton is highly photosensitive, and the chemically adsorbed molecule has an appropriate length, which results in a desirable alignment control performance. In addition, the compound is easy to synthesize.

v) The above-described method of producing a chemical adsorbate compound may be such that n in the chemical formula 101 is in the range of 5 to 10, and X is chlorine.

Accordingly, the same advantageous effects as described in the forgoing ii) can be achieved.

Further accounts of the first group of the invention are given below. The chemical adsorbate compound in accordance with the first group of the invention was accomplished based on the view that the chalcone skeleton is highly photosensitive. The chemical adsorbate compound is characterized in that a carbonyl group is bonded at the 4' position of the benzene ring in the chalcone skeleton, a divalent functional group (preferably a linear hydrocarbon group) having an appropriate length is bonded to the carbonyl group, and an —O—SiX group (where X is a halogen) is bonded to one end of the divalent functional group.

The value n of the hydrocarbon group $(CH_2)_n$ in the chemical formula 101 should be an integer from 1 to 20, preferably in the range of 3 to 16, more preferably in the range of 5 to 10. The reason is, as already stated above, the efficiency of the crosslinking is degraded when n is either too large or too small. Accordingly, a preferred embodiment of the first group of the invention includes, for example, a compound represented by the following chemical formula 105:

Chemical Formula 105

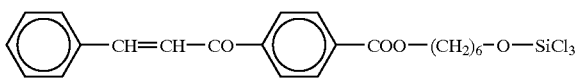

In the chemical adsorbate compound in accordance with the first group of the invention, other divalent functional groups may be employed in place of $(CH_2)_n$ in the chemical formula 101. Examples of such divalent functional groups include a divalent functional group containing a carbon-carbon double bond or a carbon-carbon triple bond in part of the hydrocarbon groups, a divalent functional group in which hydrogen in the hydrocarbon groups is substituted by other functional groups (e.g., methyl groups, methyl halide groups, hydroxyl groups, cyano groups, or the like) and/or atoms (e.g., F, Cl, Br, I, or the like), and a divalent functional group in which a C—O—C (ether) bond or a C—CO—C— (carbonyl) bond is substituted for a C—C bond in the hydrocarbon group.

The above-described chemical adsorbate compound in accordance with the first group of the invention can be produced by a method having a step of reacting benzaldehyde with 4-acetylbenzoic acid by aldol condensation. The detail of this reaction will be given in Examples to be described hereinbelow. When the method in which benzaldehyde and 4-acetylbenzoic acid are used as starting materials is employed, a desired compound can be synthesized with a good reaction efficiency. Nevertheless, the chemical adsorbate compound can be synthesized by other producing methods, and, for example, it is possible to employ such a method that, using chalcone as a starting material, a characteristic group is added thereto.

(2) The Second Group

The second group of the invention relates to a liquid crystal alignment film and a liquid crystal display device utilizing the alignment film.

i) In accordance with the second group of the invention, there is provided a liquid crystal alignment film comprising an aggregate of adsorbed molecules chemically adsorbed by siloxane bonds directly or via a layer of another substance onto a substrate having an electrode formed thereon, and each of the adsorbed molecules comprising an —O—Si bond group at an end of the molecule and a characteristic group represented by the chemical formula 201:

Chemical Formula 201

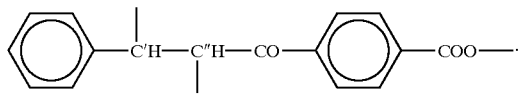

The liquid crystal alignment film of the above-described configuration is composed of an aggregate of adsorbed molecules in which one end of each adsorbed molecule (the end adjacent to the —O—Si bond group side) chemically bonds to the substrate while the other end protrudes in a direction far from the substrate surface. In the aggregate of adsorbed molecules which contain the characteristic groups of the chemical formula 201 and the —O—Si bond groups, since each individual adsorbed molecule is firmly bonded to the substrate by chemical bond, the film does not easily come off from the substrate, In addition, liquid crystal molecules can enter the gap spaces between the adsorbed molecules in the aggregate, and the inclination (pretilt angle) and alignment orientation (pretilt orientation) of the liquid crystal molecules with respect to the substrate are restricted by the inclination and/or alignment orientation (hereinafter these are also collectively referred to as an "alignment direction") of the adsorbed molecules with respect to the substrate.

Accordingly, by employing the above-described configuration of the invention, it is made possible to form a liquid crystal alignment film composed of a film in which every adsorbed molecule has an influence over the alignment control of liquid crystal molecules. Such an alignment film exhibits a remarkably high efficiency in the alignment control performance in relation to the film thickness. In addition, the resultant film has a remarkably small thickness, leading to an excellent light transmission characteristic and durability. Moreover, this film does not cause much undesirable effect as an electrically resistive film, and therefore does not hinder the electric field for driving liquid crystals. Thus, by employing the above-described configuration of the invention, a liquid crystal alignment film capable of increasing the brightness and contrast ratios and reducing the driving voltage can be realized.

An example of the adsorbed molecules comprising an —O—Si bond group and a characteristic group represented by the foregoing chemical formula 201 is a compound represented by the following chemical formula 202.

Chemical Formula 202

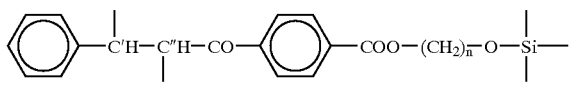

(In the formula, n is an integer from 1 to 20.)

The adsorbed molecules represented by the chemical formula 202 have an appropriate molecular length, which leads to a good alignment control over liquid crystal molecules. In addition, the resultant alignment film has excellent durability since the molecules can be firmly bonded to the substrate via Si and moreover the molecules each other can be firmly bonded via Si.

It is noted that the adsorbed molecules need to have an appropriate molecular length in order to obtain a good liquid crystal alignment performance and crosslinking performance, and accordingly, n in the hydrocarbon group $(CH_2)_n$ is preferable to be in the range of 1 to 20. Nevertheless, in terms of crosslinking performance, n is preferable to be in the range of 3 to 16, and more preferable to be in the range of 5 to 10. In order for the crosslinking to be performed with high efficiency, the relative positions of the carbon-carbon double bonds of the adsorbed molecules to be crosslinked are important, i.e., the photosensitive groups must be in contact with or adjacent to each other. However, when n is small (or example, less than 5), the angle or proportion of the adsorbed molecules arrayed vertically with respect to the substrate becomes small. In other words, many of the molecules are arrayed horizontally with respect to the substrate, and this reduces the degree of contacts at carbon-carbon double bonds (photosensitive sites), which in turn reduces the efficiency in crosslinking.

On the other hand, if n is large, (for example, greater than 10), the degree of freedom of molecules with respect to the substrate material surface becomes too large, which reduces the degree of contacts at the photosensitive sites in the adsorbed molecules each other. Thus, the efficiency of the crosslinking also decreases in this case, and consequently, the resultant film shows a small crosslinking rate.

In the aggregate of adsorbed molecules that constitutes the liquid crystal alignment film, the adsorbed molecules may be aligned in a predetermined direction. Thereby, a uniform liquid crystal alignment performance is obtained.

In the above-described alignment film, and an inclination and/or alignment direction of long axes of the adsorbed molecules with respect to a substrate surface plane may be different in a plurality of divided domains next to each other. The plurality of divided domains refers to a plurality of micro-domains such that a single pixel region is divided into a plurality of domains in a pattern-like manner. When such a so-called multi-domain type liquid crystal alignment film, in which the alignment direction of the adsorbed molecules is controlled in each of the micro-domains, is employed, a viewing angle dependency in displayed images is reduced since the transmitted light in each pixel is made up of a plurality of bundles of lights.

In the above-described alignment film, the adsorbed molecules may be crosslinked with each other at the carbon C' and/or the carbon C" in the chemical formula 201 or 202. In the aggregate of adsorbed molecules, the inclination and alignment direction of the adsorbed molecules are not varied by external degrading factors such as heat or friction since the adsorbed molecules are firmly bonded each other by crosslinking. Accordingly, a highly reliable liquid crystal alignment film can be obtained.

In the above-described liquid crystal alignment film, a film thickness thereof may be from 0.5 nm to less than 10 nm. Within this thickness range, high alignment control efficiency relative to film thicknesses is achieved, and no hindrance to light transmission and electric field is caused. Thus, the utility of the film as a liquid crystal alignment film is further increased.

In the above-described liquid crystal alignment film, the liquid crystal alignment film may be a monomolecular thin film. When the film is a monomolecular thin film, the efficiency in liquid crystal alignment control remarkably increases since every individual adsorbed molecule can directly influence the alignment of liquid crystal molecules.

Next, detailed below are methods for producing liquid crystal alignment films in accordance with the second group of the invention. In one embodiment of the second group of the invention, there is provided a method for producing a liquid crystal alignment film comprising at least the steps of preparing a chemisorption solution by dissolving in a non-aqueous solvent a chemical adsorbate compound having an —O—Si bond group at a molecular end and a characteristic group represented by the chemical formula 203:

Chemical Formula 203

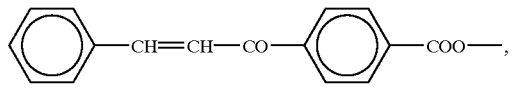

and contacting the chemisorption solution with a substrate surface having a pixel electrode formed thereon to adsorb molecules of the chemical adsorbate compound in the chemisorption solution onto the substrate surface by siloxane bonds.

The above-described method may further comprise a step of drain-drying including, after the step of contacting the chemisorption solution, rinsing the substrate surface having the adsorbed molecules thereon with a nonaqueous solvent for cleaning, and draining and drying the solvent for cleaning remaining on the substrate surface in a predetermined direction. In addition, the above-described method may further comprise, after the step of drain-drying, irradiating the adsorbed molecules on the substrate surface with a polarized ultraviolet light so that the adsorbed molecules are crosslinked with each other at a carbon-carbon double bond shown in the chemical formula 203.

Further, the above-described method may be such that the steps of drain-drying and irradiating with a polarized ultraviolet light are repeated a plurality of times, the direction of the draining and drying is varied each time of the step of drain-drying, and one of a) a region to be irradiated with the ultraviolet light and a direction of the ultraviolet light, b) a region to be irradiated with the ultraviolet light and an incident angle of the ultraviolet light, and c) a region to be irradiated with the ultraviolet light, a direction of the ultraviolet light, and an angle of applying the ultraviolet light, is varied each time of the step of irradiating, whereby an inclination and/or alignment direction of long axes of the adsorbed molecules is/are varied in a plurality of domains such that a single pixel region is divided into the plurality of domains in a pattern-like manner. Accordingly, a multi-domain type liquid crystal alignment film can be efficiently fabricated with a high productivity.

Further in the above-described method, an aprotic solvent may be used for the nonaqueous solvent for cleaning in the step of rinsing, whereby unreacted chemical adsorbate compound is removed by rinsing the substrate surface to form a monomolecular thin film.

Further in the above-described method, a mixed solvent of an aprotic solvent and a protic solvent may be used for the nonaqueous solvent for cleaning in the step of rinsing, whereby unreacted chemical adsorbate compound is removed by rinsing the substrate surface to form a monomolecular thin film. The mixed solvent of an aprotic solvent and a protic solvent is preferable in that the capability of dissolving the chemical adsorbate compound and the evaporation rate can be appropriately controlled.

The significance of the above-described methods is now discussed below. When the substrate is contacted with the solution of the chemical adsorbate compound having the characteristic group represented by the chemical formula 203 and the —O—Si bond group at a molecular end, there is formed a thin film in which the chemical adsorbate compound is bonded to hydrophilic groups on the substrate surface by siloxane bonds (this is also referred to as "chemical adsorption"). The thin film is composed of an aggregate of adsorbed molecules aligned in such a manner that one longitudinal end (the end adjacent to the —O—Si bond group) of each adsorbed molecule is chemically bonded to the substrate while the other end is extended towards a direction far from the substrate surface. In such a thin film composed of the aggregate of the adsorbed molecules, liquid crystal molecules can enter the gap spaces between the adsorbed molecules. The inclination (pretilt angle) and alignment orientation (pretilt orientation) of the liquid crystal molecules slotted in the gap spaces with respect to the substrate are restricted by the inclination and/or alignment orientation (hereafter these are also collectively referred to as an "alignment direction") of the adsorbed molecules with respect to the substrate. Thus, by specifying the alignment direction of the adsorbed molecules, the alignment direction of the liquid crystal molecules can be controlled.

In the visible light range, the compound having the characteristic group represented by the chemical formula 203 is colorless, transparent, and chemically stable, while the carbon-carbon double bond thereof is highly sensitive to ultraviolet light. Accordingly, by irradiating the substrate with ultraviolet light, the adsorbed molecules can be crosslinked with each other via the carbon-carbon double bonds after the chemical adsorbate compound is chemically adsorbed onto the substrate. When a polarized ultraviolet light is used in this step, the direction of crosslinking can be controlled to a certain direction corresponding to the direction of polarization of the polarized ultraviolet light. By the polarized light irradiation, the adsorbed molecules on the substrate surface are realigned. By this realignment, the molecules each other are crosslinked, and consequently, the resultant alignment film is not easily changed by external degrading factors such as heat or friction.

In the above-described method, the chemical adsorbate compound having an —O—Si bond group and a characteristic group represented by the foregoing chemical formula 203 may be a compound represented by the following chemical formula 204.

Chemical Formula 204

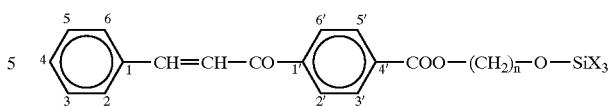

(In the formula, n is an integer from 1 to 20, and X is a halogen.)

The compound represented by the chemical formula 204 can be easily and firmly adsorbed onto the substrate surface, and the photosensitivity of the carbon-carbon double bond is high. The resultant thin film formed by the compound being chemically adsorbed exhibits excellent transparency and durability. Moreover, the compound has an appropriate molecular length for controlling the alignment of liquid crystal molecules. Hence, by employing the compound of the chemical formula 204 in the above-described method, a desirable liquid crystal alignment film can be produced with high productivity.

Some characteristic points in the above-described methods are further detailed below. In the step of drain-drying according to the methods of the invention, first, by rinsing, unadsorbed chemical adsorbate compound excessively existing on the substrate surface is removed therefrom, and thereafter, by draining and drying, the solution for cleaning is removed. By these procedures, a monomolecular thin film can be formed such that the adsorbed molecules are aligned in a direction of drain-drying. The alignment state of the adsorbed molecules thus obtained by the drain-drying can be varied by repeating the drain-drying, and is susceptible to external degrading factors (such as heat or friction). Accordingly, the alignment state thus obtained is referred to as a "pre-alignment" herein.

It is noted that examples for the methods for the draining and drying include a method by pulling up the substrate being soaked in the cleaning solution at a predetermined angle, and a method by blowing an air current onto the substrate surface from a predetermined direction.

In the above-described step of irradiating, the thin film surface (aggregate of the adsorbed molecules) is irradiated with a polarized ultraviolet light. Since the adsorbed molecules comprising the characteristic group represented by the chemical formula 203 are highly photosensitive, the molecules are reacted and crosslinked with each other at the carbon-carbon double bonds in a certain direction corresponding to the direction of polarization. The direction of polarization may be the same direction as the direction of the pre-alignment described above, or may be a different direction therefrom. In either case, by applying a polarized light, the adsorbed molecules can be realigned in a certain direction corresponding to the direction of polarization. It is, however, preferable that the direction of drain-drying and the direction of polarization not be crossed at 90°, but be staggered a little, preferably by several degrees or more. This is because, if the directions are crossed at 90°, the molecules are randomly aligned in two directions.

While the mechanism is not entirely understood, it has been confirmed by experiments that by pre-aligning the adsorbed molecules and thereafter irradiating with polarized ultraviolet light, the crosslinking is smoothly performed in a certain direction and the effect of the alignment treatment by the polarized ultraviolet irradiation is enhanced.

It is to be noted that the alignment by the polarized ultraviolet light irradiation is referred to as a "realignment" herein, in order to distinguish it from the pre-alignment described above. It is also to be noted that the compound molecules after being chemically adsorbed onto the substrate are referred to as "adsorbed molecules," and the compound before being adsorbed are referred to as "chemical adsorbate compound." In addition, it has been confirmed by experiments that the thickness of the thin film in which the adsorbed molecules are chemically adsorbed onto the substrate surface is approximately the molecular length of the adsorbed molecule (in the order of nanometers).

The differences between the liquid crystal alignment films according to the present invention and conventional liquid crystal alignment films are as follows. In the conventional liquid crystal alignment films (for example, polymer films composed of polyimides mentioned above), the long main chains are densely intertwined each other, and consequently, only the surface portion of the films can contribute to the alignment control over liquid crystals. For this reason, the conventional alignment films cannot achieve a sufficient alignment control performance. Moreover, in conventional alignment films in which the alignment control characteristic is obtained by rubbing, the alignment control characteristic is changed or degraded by external degrading factors such as hear or friction. Furthermore, polymer films composed of such as polyimides can hinder the light transmission and driving of liquid crystal since such films have a large film thickness and high electrical resistivity.

Nonetheless, even when the liquid crystal alignment film is made of a monomolecular thin film, the alignment stability can be insufficient if the adsorbed molecules are not crosslinked with each other. For example, the foregoing chemical adsorbate compound disclosed in Japanese Unexamined Patent Publication No. 3-7913 does not have a photoreactive group, and therefore is not capable of chemically linking the adsorbed molecules each other. Therefore, in the liquid crystal alignment films employing this chemical ad sorbate compound, the alignment control characteristic tends to be degraded by heat at about 200° C.

Next, liquid crystal display devices according to the second group utilizing the above-described alignment films are described below.

In one embodiment of the second group of the invention, there is provided a liquid crystal display device comprising a pair of opposed substrates, a liquid crystal alignment film provided on a surface of at least one of the substrates, the surface having an electrode thereon, and a liquid crystal enclosed in a cell gap between the pair of substrates, the liquid crystal display device wherein the liquid crystal alignment film comprises an aggregate of adsorbed molecules chemically adsorbed directly or via a layer of another substance onto the surface of the substrate having an electrode thereon by siloxane bonds, and each of the adsorbed molecules comprises an —O—Si bond group at an end of the molecule and a characteristic group represented by the chemical formula 201:

Chemical Formula 201

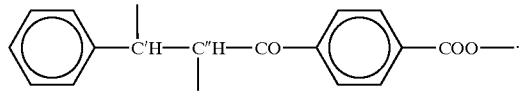

In the above-described liquid crystal display device, a pretilt angle and/or pretilt orientation of liquid crystal molecules in the cell gap may be controlled by an inclination and/or alignment direction of long axes of the adsorbed molecules with respect to a substrate surface plane.

In addition, the above-described liquid crystal display device may be such that the liquid crystal alignment film has a plurality of domains such that a single pixel region is divided into the plurality of domains in a pattern-like manner, and an inclination and/or alignment direction of long axes of the adsorbed molecules with respect to a substrate surface plane is/are different in the plurality of domains next to each other.

In another embodiment of the second group, there is provided an in-plane switching type liquid crystal display device comprising a substrate, a pixel electrode provided on the substrate, a counter electrode also provided on the substrate on which the pixel electrode is provided, and a liquid crystal alignment film formed on a surface of the substrates on which both of the electrodes are provided; the liquid crystal display device wherein the liquid crystal alignment film comprises an aggregate of adsorbed molecules chemically adsorbed directly or via a layer of another substance onto the surface of the substrate having the electrode thereon by siloxane bonds, and each of the adsorbed molecules comprises an —O—Si bond group at an end of the molecule and a characteristic group represented by the foregoing chemical formula 201.

In the above-described liquid crystal display device (hereafter including the in-plane switching type where applicable), a pretilt angle and/or pretilt orientation of liquid crystal molecules in the cell gap may be controlled by an inclination and/or alignment direction of long axes of the adsorbed molecules with respect to a substrate surface plane.

In the above-described liquid crystal display device, the adsorbed molecules may be crosslinked with each other at the carbon C' and/or the carbon C" in the chemical formula 201.

In the above-described liquid crystal display device, each of the adsorbed molecules may be composed of a compound represented by the chemical formula 202:

Chemical Formula 202

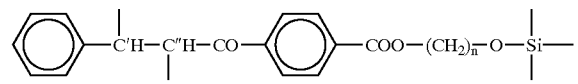

(In the formula, n is an integer from 1 to 20.).

In the above-described liquid crystal display device, a film thickness of the liquid crystal alignment film may be from 0.5 nm to less than 10 nm.

In the above-described liquid crystal display device, the liquid crystal alignment film may be a monomolecular thin film.

It is considered that in an ideal monomolecular layer, each single constituent molecule is arrayed along a substrate surface and no molecules are overlaid thereon. However, in practice, it is not so easy to form a perfect monomolecular layer, and moreover, a monomolecular layer that is not so perfect can sufficiently accomplish the objects of the invention. Accordingly, it is to be understood that a monomolecular thin film according to the present invention may be such a thin film that it is recognized as a substantially monomolecular layer. For example, it may be such a film partially having a layer of a plurality of molecules in which unadsorbed molecules are overlaid on the adsorbed molecules onto a substrate. Also included is such a film partially having a layer of a plurality of molecules in which molecules that are themselves unbonded to the substrate but bonded to the molecules already fixed to the substrate, or further other molecules are bonded to the unbonded molecules. It is to be understood that monomolecular thin films according to the present invention includes these films partially having a layer of a plurality of molecules.

In addition, although the above discussion has been made based on the premise that an aggregate of adsorbed molecules is composed only of one type of chemical adsorbate compound, it is to be understood that other adsorbate compounds may be mixed with the adsorbed molecules of the present invention.

(3) The Third Group i) In accordance with the third group of the invention, there is provided a chemical adsorbate compound represented by the following chemical formula 301. It is noted that a chalcone skeleton means a skeleton represented by the following chemical formula 304.

Chemical Formula 301

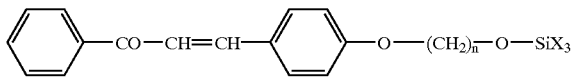

(In the formula, n is an integer from 1 to 20, and X is a halogen.)

Chemical Formula 304

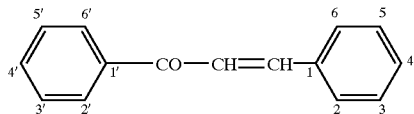

The compound having a chemical structure shown by the chemical formula 301, —O—SiX$_3$ serves as a chemically adsorbed group. Therefore, the compound can be easily adsorbed onto a surface of a substrate material having hydrophilic groups (for example, OH groups, COOH groups, NH$_2$ groups, NH groups, SH groups, etc.). Thus, a monomolecular film having an extremely small thickness can be easily formed on the substrate material surface. The compound having a chemical structure represented by the chemical formula 301 is colorless, transparent, and chemically stable in the visible light range.

In addition, the compound of the chemical formula 301 has a carbon-carbon double bond in the molecular structure, and a linear hydrocarbon group is ether-linked to the 4' position of the benzene ring in the chalcone skeleton in the compound. In the compound having such a chemical structure, the ether-linked linear hydrocarbon group serves to increase the density of the conjugated electrons delocalized and stabilized in the chalcone skeleton. The compound is thereby further stabilized, and the ultraviolet absorption wavelength derived from the electrons is further shifted towards a longer wavelength range. As a result, the compound has an absorption peak in the longer wavelength range. Thus, by irradiating the compound with an ultraviolet light having a wavelength in the long wavelength range near the visible range, the electrons at the carbon-carbon double bond in the chalcone skeleton are excited and activated, and the adsorbed molecules can be crosslinked with each other via the bonds. Here, if a long wavelength ultraviolet light is employed, a good film can be obtained since such an ultraviolet light does not easily cause a side reaction (decomposition). The resultant film exhibits excellent durability and abrasion resistance, as well as excellent chemical stability, transparency, and water repellency.

From the above discussion, it will be understood that the compound represented by the chemical formula 301 is useful as a functional film for modifying the surface of a substrate material, and particularly useful in forming a liquid crystal alignment film. The reasons why the film formed of the compound is suitable for a liquid crystal alignment film will now be discussed below.

The chemical adsorbate compound of the chemical formula 301 is easily chemically bonded to the substrate material surface. Therefore, when the solution containing the chemical adsorbate compound of the chemical formula 301 (chemisorption solution) contacts with the surface of the substrate as a component of a liquid crystal cell, one end of each adsorbed molecule (the end adjacent to the —O—Si bond group) chemically is bonded to the substrate while the other end protrudes in a direction far from the substrate surface. Thereby, it is made possible to form a thin film composed of an aggregate of a multiplicity of the adsorbed molecules arrayed along the substrate surface. In such a thin film composed of the aggregate of the adsorbed molecules, liquid crystal molecules can enter the gap spaces between the adsorbed molecules. The inclination (pretilt angle) and alignment orientation (pretilt orientation) of the liquid crystal molecules slotted in the gap spaces with respect to the substrate are controlled by the inclination and/or alignment orientation (hereinafter these are also collectively referred to as an "alignment direction") of the adsorbed molecules with respect to the substrate. Thus, by controlling the alignment direction of the adsorbed molecules, the alignment direction of the liquid crystal molecules can be arbitrarily controlled.

In addition, the resultant film is a monomolecular film having an extremely small thickness and therefore shows excellent light transmission characteristic. Further, the resultant film exhibits a remarkably high efficiency in the alignment control performance since every individual adsorbed molecules has an influence on the alignment control over liquid crystal molecules. Moreover, since the film is not made of polymer, the adverse effects as an electrical resistive/insulative film are small, and the film does not hinder the electric field for driving liquid crystals. Furthermore, since the adsorbed molecules in the thin film are firmly bonded to the substrate by chemical bond, the film does not easily come off from the substrate surface.

By applying a polarized ultraviolet light to the above-described film, the adsorbed molecules can be crosslinked with each other in a certain direction at the carbon-carbon double bonds. Thereby, a liquid crystal alignment film having a desired alignment control characteristic can be attained without rubbing. The resultant alignment film is chemically stabilized and therefore the alignment control characteristic is not varied by external degrading factors such as heat or friction. Hence, an advantageous non-rubbed liquid crystal alignment film can be formed by employing the above chemical adsorbate compound, and a liquid crystal display device capable of driving liquid crystal at a low voltage and having an excellent brightness and contrast ratio can be realized by utilizing the liquid crystal alignment film.

It is considered that crosslinking of the molecules serves to stabilize the liquid crystal alignment control characteristic since the configuration of the molecules each other becomes stabilized by the crosslinking of the adsorbed molecules with each other. By contrast, in conventional rubbed liquid crystal alignment films, the alignment control changes by external factors such as heat or friction, which is apparent from the fact that repeating the rubbing causes a change in the characteristic. Also, since conventional liquid crystal alignment films made of polymers such as polyimides have such a structure that long main chains are densely intertwined each other, and only the surface portion of the films can contribute to the alignment control over liquid crystals. Consequently, conventional alignment films cannot achieve a sufficient alignment control performance. Further, conventional alignment films do not have a sufficient light transmission characteristic since they have large film thicknesses, and still further, they have a large electrical insulating characteristic, which necessitates a higher driving voltage.

ii) In the foregoing chemical adsorbate compound represented by the chemical formula 301, n may be an integer from 5 to 10 and X may be chlorine in the chemical formula 301.

If n in the chemical formula 301 is less than 5, in other words, if the length of the hydrocarbon group is shorter than 5 C, the efficiency in the crosslinking reaction decreases. In order for the crosslinking to progress at high efficiency, the relative positions of the carbon-carbon double bonds of the adsorbed molecules to be crosslinked are important, i.e., the photosensitive sites of the adsorbed molecules must be in contact with or adjacent to each other. However, when the length of the hydrocarbon group is short, the angle of the chalcone skeletons arrayed vertically with respect to the substrate material becomes small and the number of the molecules arrayed vertically also becomes small. Thus, many of the molecules are arrayed horizontally with respect to the substrate material, and therefore the photosensitive sites do not easily come in contact with or close to each other.

On the other hand, if n is greater than 10, the degree of freedom of molecules with respect to the substrate material surface becomes too large, which also leads to the disadvantage that the photosensitive sites do not easily come in contact with or close to each other and the efficiency of the crosslinking decreases. Accordingly, it is preferable that n=5 to 10.

The X in the chemical formula 301 is preferable to be chloride. When the X is chloride, the chemical adsorbate compound can be easily chemisorbed onto the substrate material by dehydrochlorination, and in addition, the adsorbed molecules per se can be easily synthesized.

iii) In another embodiment of the third group of the invention, there is provided a method for producing a chemical adsorbate compound for forming a thin film comprising at least the steps of reacting 4-hydroxybenzaldehyde and acetophenone by aldol condensation to synthesize a first compound having an hydroxyl group at the 4 position of the benzene ring in the chalcone skeleton, the first compound represented by the chemical formula 302:

Chemical Formula 302

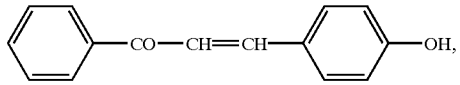

and, after the step of reacting 4-hydroxybenzaldehyde and acetophenone, reacting an alcohol derived from the first compound with an $SiX_4$ where X is a halogen in an inert gas atmosphere by dehydrohalogenation, to synthesize a second compound having at least an $—O—SiX_3$ group and a characteristic group represented by the chemical formula 303:

Chemical Formula 303

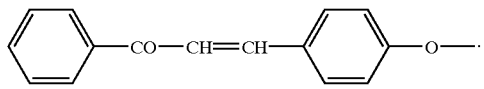

By employing this method, it is made possible to easily and efficiently produce the second compound in which the linear hydrocarbon group is ether-linked at the 4 position in the benzene ring in the chalcone skeleton and the $—SiX_3$ group is ether-linked to the hydrocarbon group. In the second compound produced by this method, the carbon-carbon double bond (—CH=CH—) in the chalcone skeleton is highly sensitive to ultraviolet light, and the $SiX_3$ has high chemical adsorbing performance.

iv) In the above-described method for producing a chemical adsorbate compound for forming a thin film, the second compound may be a compound represented by the following chemical formula 301:

Chemical Formula 301

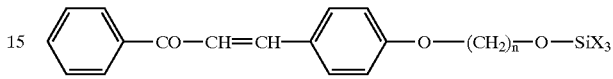

(In the formula, n is an integer from 1 to 20, and X is a halogen.)

By employing the chemical adsorbate compound composed of the compound represented by the chemical formula 301, the carbon-carbon double bond in the chalcone skeleton becomes more highly photosensitive, and the ultraviolet light absorption peak is further shifted to a longer wavelength range. Furthermore, the main axis of the molecule is linear and the molecular length is appropriate, which results in a desirable alignment control. In addition, the compound is easy to synthesize.

v) In the above-described method for producing a chemical adsorbate compound, n may be an integer from 5 to 10, and X may be chlorine in the foregoing chemical formula 301. The advantageous effects by this are the same as described above.

Further accounts of the chemical adsorbate compound in accordance with the third group of the invention are given below. The chemical adsorbate compound of the third group of the invention was accomplished based on the view that the chalcone skeleton is highly photosensitive. The chemical adsorbate compound is characterized in that, as shown in the foregoing chemical formula 301, a linear hydrocarbon group is ether-linked at the 4 position of the benzene ring in the chalcone skeleton, and an —O—SiX group (where X is a halogen) is attached thereto.

The value n of the hydrocarbon group $(CH_2)_n$ in the chemical formula 301 should be an integer from 1 to 20, preferably in the range of 3 to 16, more preferably in the range of 5 to 10. The reason is, as already stated above, the efficiency of the crosslinking is degraded when n is either too large or too small. Accordingly, a preferred embodiment of the third group of the invention includes, for example, a compound represented by the following chemical formula 305;

Chemical Formula 305

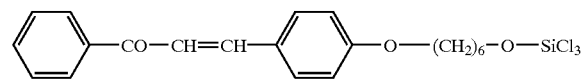

The above-described chemical adsorbate compound in accordance with the third group of the invention can be produced by a method having a step of reacting 4-hydroxybenzaldehyde and acetophenone by aldol condensation so as to bond a hydroxyl group to the 4 position of the benzene ring in the chalcone skeleton. The detail of this reaction will be given in Examples to be described hereinbelow. When the method comprising at least the steps of reacting 4-hydroxybenzaldehyde and acetophenone by aldol condensation, and reacting an alcohol having a chalcone skeleton group with an $SiX_4$ where X is a halogen in an inert gas atmosphere by condensation to synthesize a compound having an —O—$SiX_4$ bond, a desired compound can be synthesized with a good reaction efficiency. Nevertheless, the chemical adsorbate compound can be synthesized by other producing methods, and, for example, it is possible to employ such a method that, using chalcone as a starting material, a characteristic group is added thereto.

In the chemical adsorbate compound in accordance with the third group of the invention, other divalent functional groups may be employed in place of $(CH_2)_n$ in the chemical formula 301. Examples of such divalent functional groups include a divalent functional group containing a carbon-carbon double bond or a carbon-carbon triple bond in part of the hydrocarbon groups, a divalent functional group in which hydrogen in the hydrocarbon groups is substituted by other functional groups (e.g., methyl groups, methyl halide groups, hydroxyl groups, cyano groups, or the like) and/or atoms (e.g., F, Cl, Br, I, or the like), and a divalent functional group in which a C—O—C (ether) bond or a C—CO—C— (carbonyl) bond is substituted for a C—C bond in the hydrocarbon group.

(4) The Fourth Group

The foregoing and other objects of the present invention are accomplished, in accordance with the fourth group of the invention, by the provision of a liquid crystal alignment film comprising an aggregate of adsorbed molecules chemically adsorbed directly or via a layer of another substance onto a substrate having an electrode formed thereon, and each of the adsorbed molecules comprising an Si bond group at an end of the molecule and a characteristic group represented by the chemical formula 401:

Chemical Formula 401

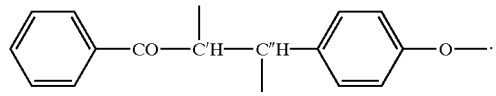

The liquid crystal alignment film of the above-described configuration is composed of an aggregate of adsorbed molecules in which one end of each adsorbed molecule (the end adjacent to the Si bond group) chemically bonds to the substrate while the other end protrudes in a direction far from the substrate surface. In the thin film composed of such an aggregate of the adsorbed molecules, since each individual adsorbed molecule is firmly bonded to the substrate by chemical bond, the film does not easily come off from the substrate. In addition, liquid crystal molecules can enter the gap spaces between the adsorbed molecules in the aggregate, and the inclination (pretilt angle) and alignment orientation (pretilt orientation) of the liquid crystal molecules with respect to the substrate are restricted by the inclination and/or alignment orientation (hereinafter these are also collectively referred to as an "alignment direction") of the adsorbed molecules with respect to the substrate. Accordingly, by employing the above-described configuration of the invention, it is made possible to form a liquid crystal alignment film composed of a film in which every adsorbed molecule has an influence on the alignment control of liquid crystal molecules. Such an alignment film exhibits a remarkably high efficiency in the alignment control performance in relation to the film thickness. In addition, the resultant film has a remarkably small thickness, leading to an excellent light transmission characteristic and durability.

Moreover, this film does not cause much undesirable effect as an electrically resistive film, and therefore does not hinder the electric field for driving liquid crystals.

Thus, by employing the above-described configuration of the invention, it is made possible to form a liquid crystal alignment film capable of improving the display characteristics of a liquid crystal display such as a brightness and contrast ratio, and reducing the driving voltage.

An example of the adsorbed molecules comprising an—Si bond group and a characteristic group represented by the foregoing chemical formula 401 is a compound represented by the following chemical formula 402.

Chemical Formula 402

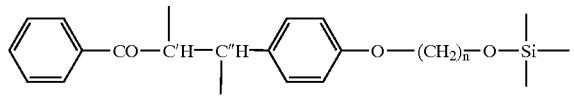

(In the formula, n is an integer from 1 to 20.)

The adsorbed molecules represented by the chemical formula 402 have an appropriate molecular length because of the linear hydrocarbon group, which leads to a good alignment control over liquid crystal molecules. In addition, the resultant alignment film has excellent durability and adhesiveness to the substrate since the molecules are firmly bonded to the substrate via Si and moreover the molecules each other are also bonded via the remaining Si sites, It is noted that the adsorbed molecules need to have an appropriate molecular length in order to obtain a good liquid crystal alignment performance and crosslinking performance. In order for the crosslinking to be performed with high efficiency, the relative positions of the carbon-carbon double bonds of the adsorbed molecules to be crosslinked are important, i.e., the photosensitive groups must be in contact with or adjacent to each other. However, when n is small (for example, less than 5), the angle or proportion of the adsorbed molecules arrayed vertically with respect to the substrate becomes small. In other words, many of the molecules are arrayed horizontally with respect to the substrate, and this reduces the degree of contacts at carbon-carbon double bonds (photosensitive sites), which in turn reduces the efficiency in crosslinking.

On the other hand, if n is large, (for example, greater than 10), the degree of freedom of molecules with respect to the substrate material surface becomes too large, which reduces the degree of contacts at the photosensitive sites in the adsorbed molecules each other. Thus, the efficiency of the crosslinking also decreases in this case, and consequently, the resultant film shows a small crosslinking rate. Accordingly, n in the hydrocarbon group $(CH_2)_n$ is preferable to be in the range of 1 to 20. Nevertheless, in terms of crosslinking performance, n is preferable to be in the range of 3 to 16, and more preferable to be in the range of 5 to 10.

In the aggregate of adsorbed molecules that constitutes the liquid crystal alignment film, the adsorbed molecules may be aligned in a predetermined direction. Thereby, a uniform liquid crystal alignment performance is obtained.

In the above-described alignment film, and an inclination and/or alignment direction of long axes of the adsorbed molecules with respect to a substrate surface plane may be different in a plurality of divided domains next to each other. Thereby, the problem of viewing angle dependency in liquid crystal displays is resolved since the transmitted light in each pixel is made up of a plurality of bundles of lights.

In the above-described alignment film, the adsorbed molecules may be crosslinked with each other at the carbon C' and/or the carbon C" in the chemical formula 401 or 402. In the aggregate of adsorbed molecules, the inclination and alignment direction of the adsorbed molecules are not varied by external degrading factors such as heat or friction since the adsorbed molecules are firmly bonded each other by crosslinking. Accordingly, a highly reliable liquid crystal alignment film can be obtained.

In the above-described liquid crystal alignment film, a film thickness thereof may be from 0.5 nm to less than 10 nm. Within this thickness range, high alignment control efficiency relative to film thicknesses is achieved, and no hindrance to light transmission and electric field is caused. Thus, the utility of the film as a liquid crystal alignment film is further increased.

In the above-described liquid crystal alignment film, the liquid crystal alignment film may be a monomolecular thin film. When the film is a monomolecular thin film, the efficiency in liquid crystal alignment control remarkably increases since every individual adsorbed molecule can directly influence the alignment of liquid crystal molecules.

ii) Next, methods for producing liquid crystal alignment films in accordance with the fourth group of the invention are described below.

In one embodiment of the fourth group of the invention, there is provided a method for producing a liquid crystal alignment film comprising at least the steps of preparing a chemisorption solution by dissolving in a non-aqueous solvent a chemical adsorbate compound represented by the chemical formula 403:

Chemical Formula 403

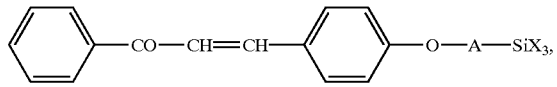

where A is a divalent functional group and X is a halogen; and contacting the chemisorption solution with a substrate surface having a pixel electrode formed thereon to adsorb molecules of the chemical adsorbate compound in the chemisorption solution onto the substrate surface.

The above-described method may further comprise, after the step of drain-drying, irradiating the adsorbed molecules on the substrate surface with a polarized ultraviolet light so that the adsorbed molecules are crosslinked with each other at a carbon-carbon double bond shown in the chemical formula 403.

Further, the above-described method may be such that the steps of drain-drying and irradiating with a polarized ultraviolet light are repeated a plurality of times, the direction of the draining and drying is varied each time of the step of drain-drying, and one of a) a region to be irradiated with the ultraviolet light and a direction of the ultraviolet light, b) a region to be irradiated with the ultraviolet light and an incident angle of the ultraviolet light, and c) a region to be irradiated with the ultraviolet light, a direction of the ultraviolet light, and an angle of applying the ultraviolet light, is varied each time of the step of irradiating, whereby an inclination and/or alignment direction of long axes of the adsorbed molecules is/are varied in a plurality of domains such that a single pixel region is divided into the plurality of domains in a pattern-like manner. Accordingly, a multi-domain type liquid crystal alignment film can be efficiently fabricated with a high productivity.

Further in the above-described method, an aprotic solvent may be used for the nonaqueous solvent for cleaning in the step of rinsing, whereby unreacted chemical adsorbate compound is removed by rinsing the substrate surface to form a monomolecular thin film.

Further in the above-described method, a mixed solvent of an aprotic solvent and a protic solvent may be used for the nonaqueous solvent for cleaning in the step of rinsing, whereby unreacted chemical adsorbate compound is removed by rinsing the substrate surface to form a monomolecular thin film. The mixed solvent of an aprotic solvent and a protic solvent is preferable in that the capability of dissolving the chemical adsorbate compound and the evaporation rate can be appropriately controlled.

In the above-described method, the chemical adsorbate compound represented by the foregoing chemical formula 403 may be a compound represented by the following chemical formula 404.

Chemical Formula 404

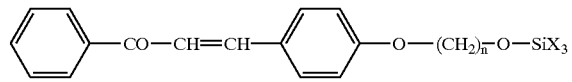

(In the formula, n is an integer from 1 to 20, and X is a halogen.)

In the compound represented by the chemical formula 404, in which A in the chemical formula 403 is $(CH_2)_n$—O— (where n is an integer from 1 to 20), the photosensitivity of the carbon-carbon double bond is high. Moreover, the compound has a desirable form (being linear and having an appropriate molecular length) for controlling the alignment of liquid crystal molecules. Hence, the compound is suitable as a material for a liquid crystal alignment film. It is noted that more preferably, n should be from 5 to 10, and X should be chlorine in the chemical formula 404.

The significance of the above-described methods is now discussed below. When the substrate is contacted with the solution of the chemical adsorbate compound represented by the above chemical formula 403 (or the chemical formula 404), there is formed a thin film in which the chemical adsorbate compound is chemically adsorbed (normally, by siloxane bonds) onto hydrophilic groups on the substrate surface. The thin film is composed of an aggregate of adsorbed molecules aligned in such a manner that one longitudinal end (the end adjacent to the —Si bond group) of each adsorbed molecule is bonded to the substrate surface while the other end is extended towards a direction far from the substrate surface. In such a thin film, liquid crystal molecules can enter the gap spaces between the adsorbed molecules. The liquid crystal molecules slotted in the gap spaces are controlled by the alignment direction of the adsorbed molecules with respect to the substrate. Thus, by specifying the alignment direction of the adsorbed molecules, the alignment direction of the liquid crystal molecules can be controlled.

In the visible light range, the compound represented by the above chemical formula 403 or the chemical formula 404 is colorless, transparent, and chemically stable, while the carbon-carbon double bond thereof is highly sensitive to ultraviolet light. Accordingly, by irradiating the substrate with ultraviolet light, the adsorbed molecules can be crosslinked with each other via the carbon-carbon double bonds after the chemical adsorbate compound is chemically adsorbed onto the substrate. When a polarized ultraviolet light is used in this step, the direction of crosslinking can be controlled in a certain direction corresponding to the direction of polarization of the polarized ultraviolet light. By the polarized light irradiation, the adsorbed molecules on the substrate surface are realigned. By this realignment, the molecules each other are crosslinked, and as a result, the resultant alignment film is not easily changed by external degrading factors such as heat or friction.

The significance of the above-described methods is further detailed below. In the step of drain-drying of the above-described methods, first, unabsorbed chemical adsorbate compound excessively existing on the substrate surface is removed therefrom by rinsing, and thereafter, the solution for cleaning is removed by draining and drying. By these procedures, a monomolecular thin film can be formed such that the adsorbed molecules are aligned in a direction of drain-drying. The alignment state of the adsorbed molecules thus obtained by the drain-drying can be varied by repeating the drain-drying. Accordingly, the alignment state thus obtained is referred to as a "pre-alignments" herein.

It is noted that examples for the methods for the draining and drying include a method by pulling up the substrate being soaked in the cleaning solution at a predetermined angle, and a method by blowing an air current onto the substrate surface from a predetermined direction. In the above-described step of irradiating, the thin film surface (aggregate of the adsorbed molecules) is irradiated with a polarized ultraviolet light. Since the adsorbed molecules comprising the characteristic group represented by the chemical formula 403 are highly photosensitive, the molecules are reacted and crosslinked with each other at the carbon-carbon double bonds in a certain direction corresponding to the direction of polarization.

While the reason is not entirely understood, it is noted that, by pre-aligning the adsorbed molecules and thereafter irradiating with polarized ultraviolet light, the crosslinking is smoothly performed in a certain direction and the effect of the alignment treatment by the polarized ultraviolet irradiation is enhanced. The direction of polarization may be the same direction as the direction of the pre-alignment described above, or may be a different direction therefrom. In either case, by applying a polarized light, the adsorbed molecules can be realigned in a certain direction corresponding to the direction of polarization. It is, however, undesirable that the direction of drain-drying and the direction of polarization are crossed at 90°. This is because, if the directions are crossed at 90°, the molecules are randomly aligned in two directions. Therefore, it is preferable that the direction of drain-drying and the direction of polarization be staggered by several degrees or more.

It is to be noted that the alignment by the polarized ultraviolet light irradiation is referred to as a "realignment" herein, in order to distinguish it from the pre-alignment described above. It is also to be noted that the compound molecules after being chemically adsorbed onto the substrate are referred to as "adsorbed molecules," and the compound before being adsorbed are referred to as "chemical adsorbate compound."

The differences between the liquid crystal alignment films according to the present invention and conventional liquid crystal alignment films are as follows. In the conventional liquid crystal alignment films (or example, polymer films composed of polyimides mentioned above), the long main chains are densely intertwined each other, and consequently, only the surface portion of the films can contribute to the alignment control over liquid crystals. For this reason, the conventional alignment films cannot achieve a sufficient alignment control performance. Moreover, in conventional alignment films in which the alignment control characteristic is obtained by rubbing, the alignment control characteristic is changed or degraded by external degrading factors such as hear or friction. Furthermore, polymer films composed of such as polyimides can hinder the light transmission and driving of liquid crystal since such films have a large film thickness and high electrical resistivity.

Nonetheless, even when the liquid crystal alignment film is made of a monomolecular thin film, the alignment stability can be insufficient if the adsorbed molecules are not crosslinked with each other. For example, the previously mentioned chemical adsorbate compound disclosed in Japanese Unexamined Patent Publication No. 3-7913 does not have a photoreactive group, and therefore is not capable of chemically linking the adsorbed molecules each other. Therefore, in the liquid crystal alignment films employing this chemical adsorbate compound, the alignment control characteristic tends to be degraded by heat at about 200° C. It is noted that it has been confirmed that the thickness of the liquid crystal alignment film of the present invention, in which the adsorbed molecules are chemically adsorbed onto the substrate surface, is approximately the molecular length of the adsorbed molecule ( in the order of nanometers).

iii) Now, liquid crystal display devices in accordance with the fourth group of the invention utilizing the above-described liquid crystal alignment films are described below.

In one embodiment of the fourth group of the invention, there is provided a liquid crystal display device comprising a pair of opposed substrates, a liquid crystal alignment film provided on a surface of at least one of the substrates, the surface having an electrode thereon, and a liquid crystal enclosed in a cell gap between the pair of substrates, the liquid crystal display device wherein the liquid crystal alignment film comprises an aggregate of adsorbed molecules chemically adsorbed directly or via a layer of another substance onto the surface of the substrate having an electrode thereon, and each of the adsorbed molecules comprises an Si bond group at an end of the molecule and a characteristic group represented by the chemical formula 401:

Chemical Formula 401

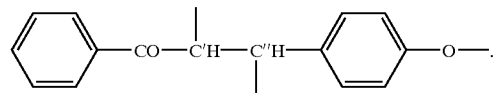

In the above-described liquid crystal display device, each of the adsorbed molecules may be composed of a compound represented by the chemical formula 402:

Chemical Formula 402

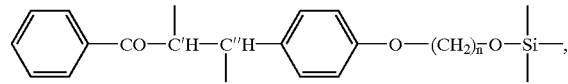

(In the formula, n is an integer from 1 to 20.)

In the above-described liquid crystal display device, a pretilt angle and/or pretilt orientation of liquid crystal molecules in the cell gap may be controlled by an inclination and/or alignment direction of long axes of the adsorbed molecules with respect to a substrate surface plane.

In another embodiment of the fourth group, there is provided an in-plane switching type liquid crystal display device comprising; a substrate, a pixel electrode provided on the substrate, a counter electrode also provided on the substrate on which the pixel electrode is provided, and a liquid crystal alignment film formed on a surface of the substrates on which both of the electrodes are provided, the liquid crystal display device wherein; the liquid crystal alignment film comprises an aggregate of adsorbed molecules chemically adsorbed directly or via a layer of another substance onto the surface of the substrate having the electrodes thereon, and each of the adsorbed molecules comprises an Si bond group at an end of the molecule and a characteristic group represented by the foregoing chemical formula 401. In addition, each of the adsorbed molecules may be composed of a compound represented by the foregoing chemical formula 402.

In the above-described liquid crystal display device (hereafter including the in-plane switching type where applicable), a pretilt angle and/or pretilt orientation of liquid crystal molecules in the cell gap may be controlled by an inclination and/or alignment direction of long axes of the adsorbed molecules with respect to a substrate surface plane.

In the above-described liquid crystal display device, the adsorbed molecules may be crosslinked with each other at the carbon C' and/or the carbon C" in the chemical formula 401 (or the chemical formula 402).

In the above-described liquid crystal display device, a film thickness of the liquid crystal alignment film may be from 0.5 nm to less than 10 nm.

In the above-described liquid crystal display device, the liquid crystal alignment film may be a monomolecular thin film. When the alignment film is a monomolecular ultra thin film, the film does not hinder the electric field for driving liquid crystal or the light transmission if disposed in the transmission light path. Accordingly, a liquid crystal display device having an excellent brightness and a reduced driving voltage can be achieved.

It is considered that in an ideal monomolecular layer, each single constituent molecule is arrayed along a substrate surface and no molecules are overlaid thereon. However, in practice, it is not so easy to form a perfect monomolecular layer, and moreover, a monomolecular layer that is not so perfect can sufficiently accomplish the objects of the invention. Accordingly, it is to be understood that a monomolecular thin film according to the present invention may be such a thin film that it is recognized as a substantially monomolecular layer. For example, it may be such a film partially having a layer of a plurality of molecules in which unadsorbed molecules are overlaid on the adsorbed molecules onto a substrate. Also included is such a film partially having a layer of a plurality of molecules in which molecules that are themselves unbonded to the substrate but bonded to the molecules already fixed to the substrate, or further other molecules are bonded to the unbonded molecules. It is to be understood that monomolecular thin films according to the present invention includes these films partially having a layer of a plurality of molecules.

In addition, although the above discussion has been made based on the premise that an aggregate of adsorbed molecules is composed only of one type of chemical adsorbate compound, it is to be understood that other adsorbate compounds and other additives may be mixed with the adsorbed molecules of the present invention.

BRIEF DESCRIPTION OF THE DRAWINGS

For a more complete understanding of the present invention, and the advantages thereof, reference is now made to the following descriptions taken in conjunction with the accompanying drawings, in which:

FIG. 6 schematically illustrates a step of applying a polarized ultraviolet light in the second group of the invention.

DESCRIPTION OF THE PREFERRED EMBODIMENTS

Figure 1:
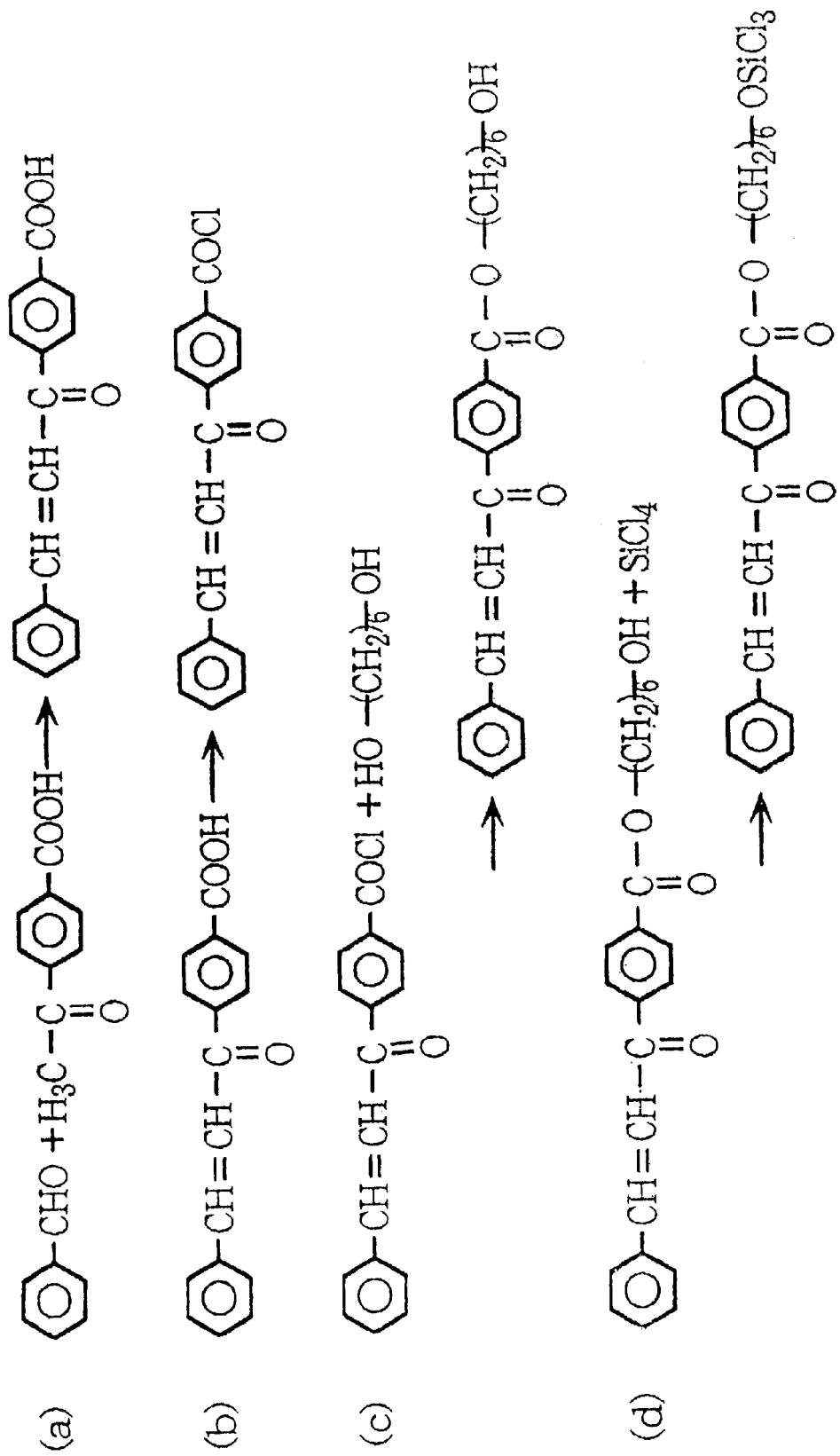
FIG. 1 shows a synthesis reaction formula of a chemical adsorbate in accordance with the first group of the invention.

Referring now to the drawings, the groups of the invention are detailed below.

Preferred Embodiments in the First Group

EXAMPLE 1-1

A method of synthesizing a novel chemical adsorbate compound in accordance with the invention is described by the following four reaction steps. The synthesized chemical adsorbate compound (silane-based chemical adsorbate compound) comprises a chalcone skeleton, a carbonyl group bonded at the 4' position of the benzene ring in the chalcone skeleton, an alkyl group $(CH_2)_6$ bonded to the carbonyl group, and an —O—Si bond group bonded to the end of the alkyl group. This chemical adsorbate compound is represented by the chemical formula 105 above.

Reaction Step 1

A 5 L reaction flask was charged with 97 g (0.92 mole) of benzaldehyde, 150.0 g (0.92 mole) of 4-acetylbenzonic acid, 22.5 g of piperidine, 22.5 ml of acetic acid, and 2.5 L of toluene. The mixture was stirred at 110° C. for 5 days and allowed to react.

The reaction solution was then cooled to room temperature, and poured into 7.5 L of 1N hydrochloric acid to precipitate crystals. The crystals were obtained by filtering, thereafter rinsed successively with water, toluene, and chloroform, and further heated and rinsed with a 45° C. chloroform/methanol=10/1 solution. Subsequently, the crystals were dried, and thus 127.0 g of 4-carboxychalcone was obtained (55.1% yield), This reaction is shown by the reaction formula in FIG. 1(a).

Reaction Step 2

A 1-L reaction vessel was charged with 80.0 g (0.32 mole) of 4-carboxychalcone and 377.7 g (3.17 mole) of thionyl chloride, and heated under reflux for 1 hour. Thereafter, thionyl chloride was removed by distilling, and thus 87.0 g of 4-(chlorocarbonyl)-chalcone was obtained (101% yield). This reaction is shown by the reaction formula in FIG. 1(b).

Reaction Step 3

Under argon current, a 5 L reaction flask was charged with 1.3 L of dry THF (dry tetrahydrofuran), 30.0 g (0.30 mole) of triethylamine, and 70.0 g (0.60 mole) of 1,6-hexanediol, and cooled to 5° C. or below, Into the reaction solution, a solution in which 80.0 g (0.30 mole) of 4-(chlorocarbonyl)-chalcone was dissolved in 800 ml of dry THF was dripped over a period of 40 minutes while the temperature of the reaction solution was maintained at 5° C. or lower.

After the resultant solution was further stirred at the same temperature for 1 hour, the reaction mixture was poured into 1.5 L of ice water, and the pH was adjusted to 3 with the use of 1N hydrochloric acid. The product was extracted with ethyl acetate, and the extracted solution was rinsed successively with water and 1N hydrochloric acid and then dehydrated with magnesium sulfate. The crude crystals thus obtained were purified with the use of silica gel column (mobile phase; n-hexane/ethyl acetate=2/1), and the purified crystals were recrystallized with ethyl acetate.

By the procedure described above, 39.4 g of (6-hydroxyhexyl)chalcone-4-carboxylate was obtained. The yield was 37.3%. The purity of the resultant material was analyzed by high-performance liquid chromatography and found to be 99%. This reaction is shown by the reaction formula in FIG. 1(c).

Reaction Step 4

Under argon current, a 300 ml reaction flask was charged with 25.0 g (0.071 mole) of (6-hydroxyhexyl)chalcone-4-carboxylate and 100 g (0.59 mole) of silicon tetrachloride, and the mixture was stirred at room temperature for 2 hours. Thereafter, excessive silicon tetrachloride was removed by distilling. Thus, 34.0 g of final product was obtained (98.6% yield). This reaction is shown by the reaction formula in FIG. 1(d).

Figure 2:
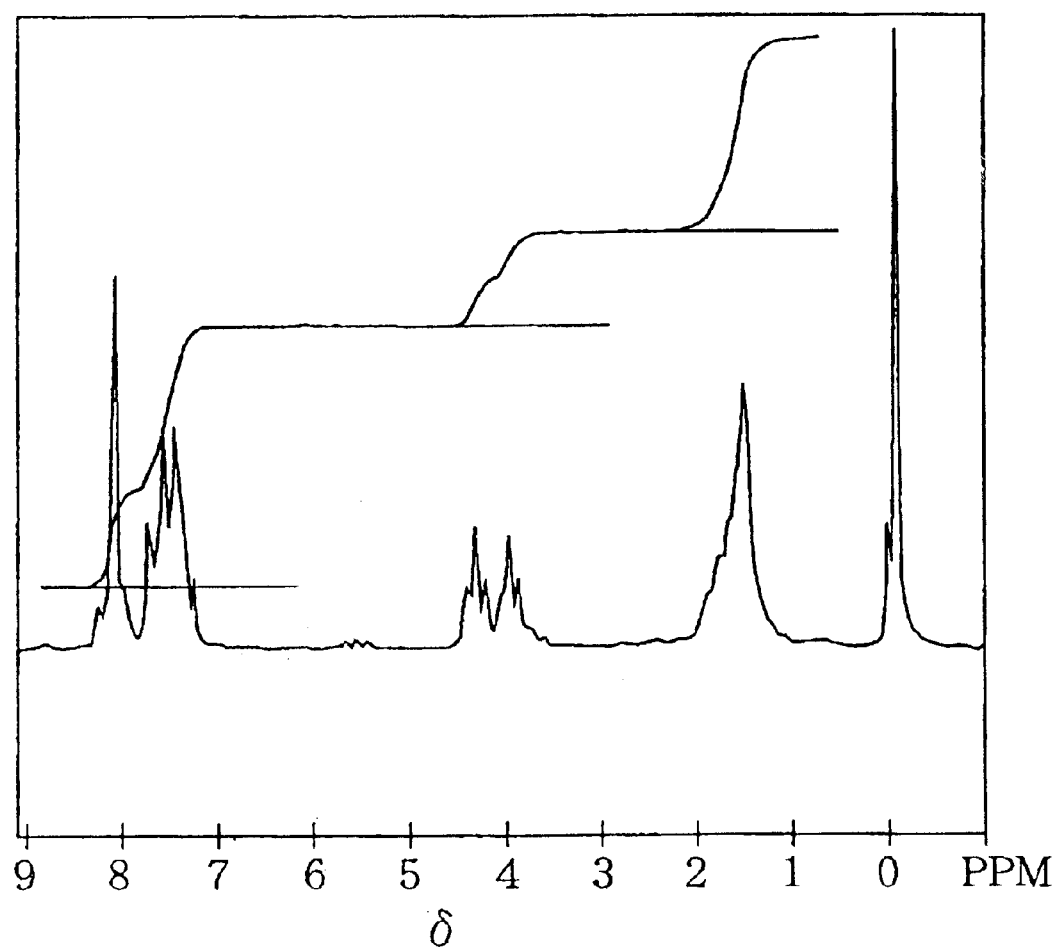
FIG. 2 is a $^1$H-NMR spectrum chart of the final product synthesized in accordance with the synthesis reaction formula in FIG. 1.

Each of the above-described products was analyzed by measuring infrared absorption spectra, MS spectra, and $^1$H-NMR. spectra. The analyses confirmed that in each of the reaction steps, the intended compounds were obtained. In FIG. 2 which illustrates the $^1$H-NMR spectrum of the final product, the peaks shown in the figure demonstrate that the final product has the chemical structure represented by the foregoing chemical formula 106.

Figure 3:
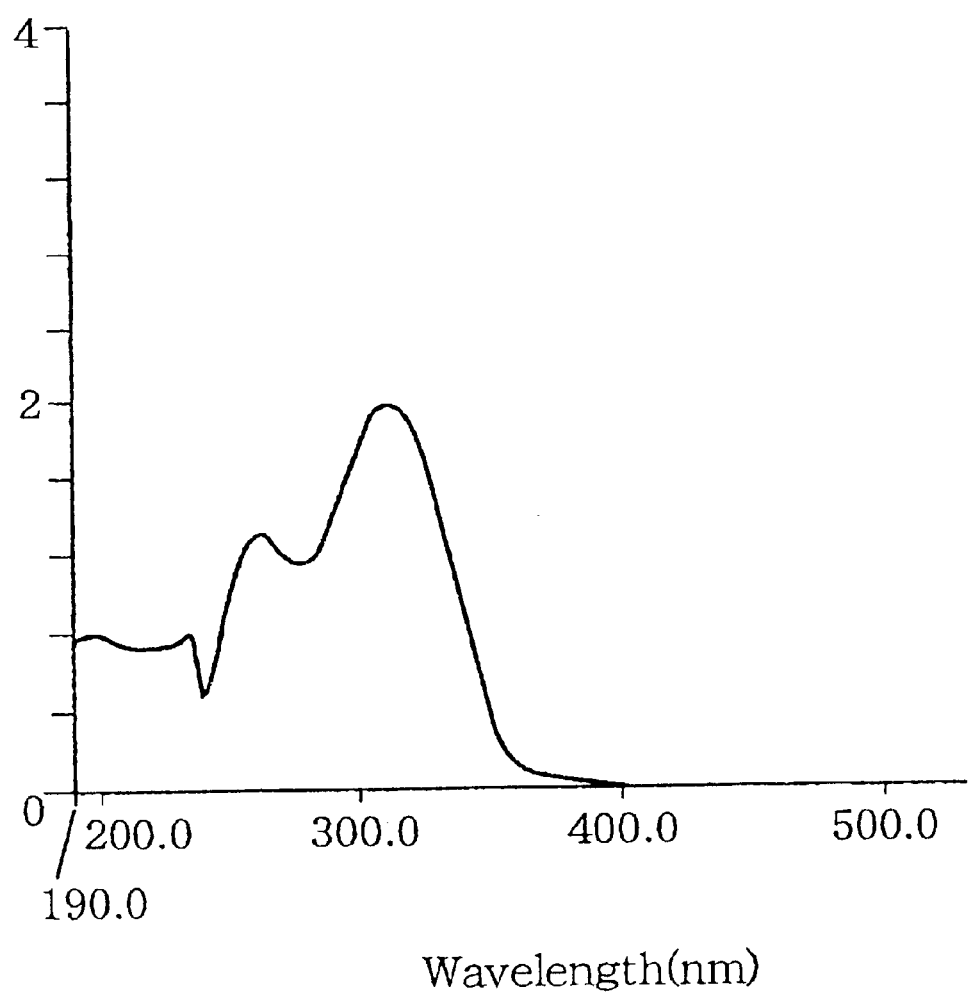
FIG. 3 is an ultraviolet-visible absorption spectrum chart of the final product synthesized in accordance with the synthesis reaction formula in FIG. 1.

Further, the final product was dissolved in chloroform, and ultraviolet-visible absorption spectrum was measured. The result is shown in FIG. 3. FIG. 3 shows that the final product has no absorption peak in the visible range, but has a first absorption peak at 312 nm, which is in the ultraviolet range, and a second absorption peak at 264 nm. This shows that the above-described chlorosilane-based chemical adsorbate compound has low sensitivity to visible light, but has high sensitivity to ultraviolet light.

It is noted that while a synthesizing method of a specific compound represented by chemical formula 105 is described here, the chemical adsorbate compound represented by the foregoing general formula 101 can be synthesized by using HO—O—$(CH_2)_n$—OH (n=1 to 20) in place of HO—$(CH_2)_6$—OH in the reaction of FIG. 1(c), and using $SiX_4$ (where X is halogen) in place of $SiCl_4$ in the reaction of FIG. 1(d).

It is also noted that, for the $^1$H-NMR spectroscopy, the IR spectroscopy, and the UV-VIS spectroscopy, R-1200 manufactured by Hitachi, Ltd., FTIR4300 manufactured by Shimadzu, Corp., UV-240 also manufactured by Shimadzu, Corp. were respectively used.

Film Formation Test

Film-forming performance of the above-described chemical adsorbate compound and characteristics of the formed film were tested by forming a film on a glass substrate using the chemical adsorbate compound. The method of forming the film was as follows. A solution was prepared by dissolving the above-described chemical adsorbate compound in a 1/9 mixed solvent of xylene/silicone (KF96L available from Shin-Etsu Chemical Co., Ltd.) to have a concentration of 0.5 wt. %. A glass substrate was soaked in the solution for about 2 hours, and thereafter the substrate was taken out of the solution. The substrate was sufficiently rinsed with chloroform while the substrate was placed in a standing position, and dried in the air. A thin film was thus formed.

The contact angle of the film with water was measured. The result was 80 degrees, which confirmed that the thin film had sufficient water repellency. In addition, the film thickness of the thin film was measured with the use of an ellipsometer (the refractive index being 1.46). The film thickness was found to be about 2.5 nm, which confirmed that a substantially monomolecular thin film was formed.

Polanrized Light Irradiation and Liquid Crystal Alignment Control Characteristic The thin film produced according to the above-described manner was subjected to a polarized light irradiation treatment in which a polarized light (312 nm wavelength, 2.5 mW/cm$^2$ light intensity) adjusted with the use of a polarizing plate was applied to the film. The thin film was then examined by UV-VIS spectroscopy before and after the polarized light irradiation. As a result, it was confirmed that an absorption peak at 312 nm almost disappeared, and the molecules were crosslinked at the position of carbon-carbon double bond (—CH=CH—) in the foregoing chemical formula 105 by the polarized light irradiation.

Meanwhile, a liquid crystal cell (hereinafter referred to as a "test cell") was prepared in the following manner. The thin film irradiated with polarized light was formed on a substrate, and the substrate with the thin film was attached to another glass plate so that the thin film was on the inside of the cell and a gap of about 12 μm was provided between the substrate and the glass plate. Then, the perimeter of the plates was sealed, and thereafter a nematic liquid crystal (ZLI4792 available from Merck & Co., Inc.) was filled into the gap. Thus, a test cell was prepared. Polarizing plates were placed on both outward surfaces of the test cell, and a liquid crystal alignment control characteristic of the thin film was examined using visible light. As a result, it was confirmed that the liquid crystal molecules in the test cell were uniformly aligned in the direction of the polarized light.

In addition, a substrate having the thin film irradiated with polarized light was heated at about 200° C. for 1 hour, and using the substrate, a test cell was prepared in the same manner as described above to examine alignment directions of the liquid crystal molecules. As a result, it was confirmed that a thermally stable alignment film can be formed by employing the above-described chemical adsorbate compound.

It is noted that the alignment state of liquid crystal can be confirmed by allowing to transmit a light from one side of the liquid crystal cell on which a polarized plate is disposed and observing the transmitted light coming out from the other side of the cell.

As seen from the above description, the novel chemical adsorbate compound in accordance with the first group of the invention has a functional group that can be firmly chemically bonded to a hydrophilic group on a surface of a substrate material, and therefore, by employing the chemical adsorbate compound, it is made possible to easily form a monomolecular thin film on the surface of the substrate material. The formed thin film is stable, colorless, and transparent in the visible light range, and also excellent in water repellency and durability. In addition, this chemical adsorbate compound has a photosensitive group, and therefore, by adsorbing the chemical adsorbate compound to the surface of the substrate material and thereafter applying a polarized ultraviolet light thereto, the adsorbate molecules can be crosslinked each other in a certain direction. Accordingly, utilizing such properties of the chemical adsorbate compound, a liquid crystal alignment film having a strong and stable liquid crystal alignment control characteristic can be produced. Hence, the chemical adsorbate compound in accordance with the first group of the invention is useful as a material for modifying a substrate material surface as well as a material for liquid crystal alignment films.

Preferred Embodiments in the Second Group

EXAMPLE 2-1

A liquid crystal alignment film of Example 2-1 is described below.

(1) Synthesis of Chemical Adsorbate Compound

A compound represented by the following chemical formula 205, which is identical to the compound represented by the foregoing chemical formula 105 in Example 1 1 was synthesized in the same manner as in Example 1-1, and this compound was employed as a chemical adsorbate compound.

Chemical Formula 205

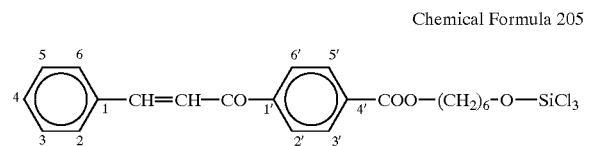

(2) Preparation of Liquid Crystal Alignment Film

Figure 4:
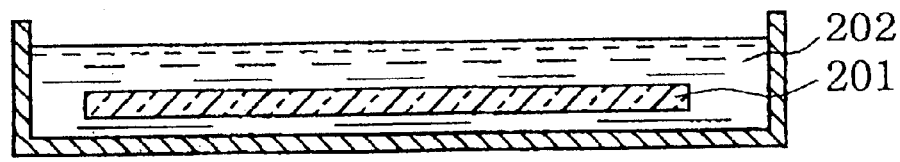
FIG. 4 schematically illustrates a chemisorption step in the second group of the invention.
Figure 5:
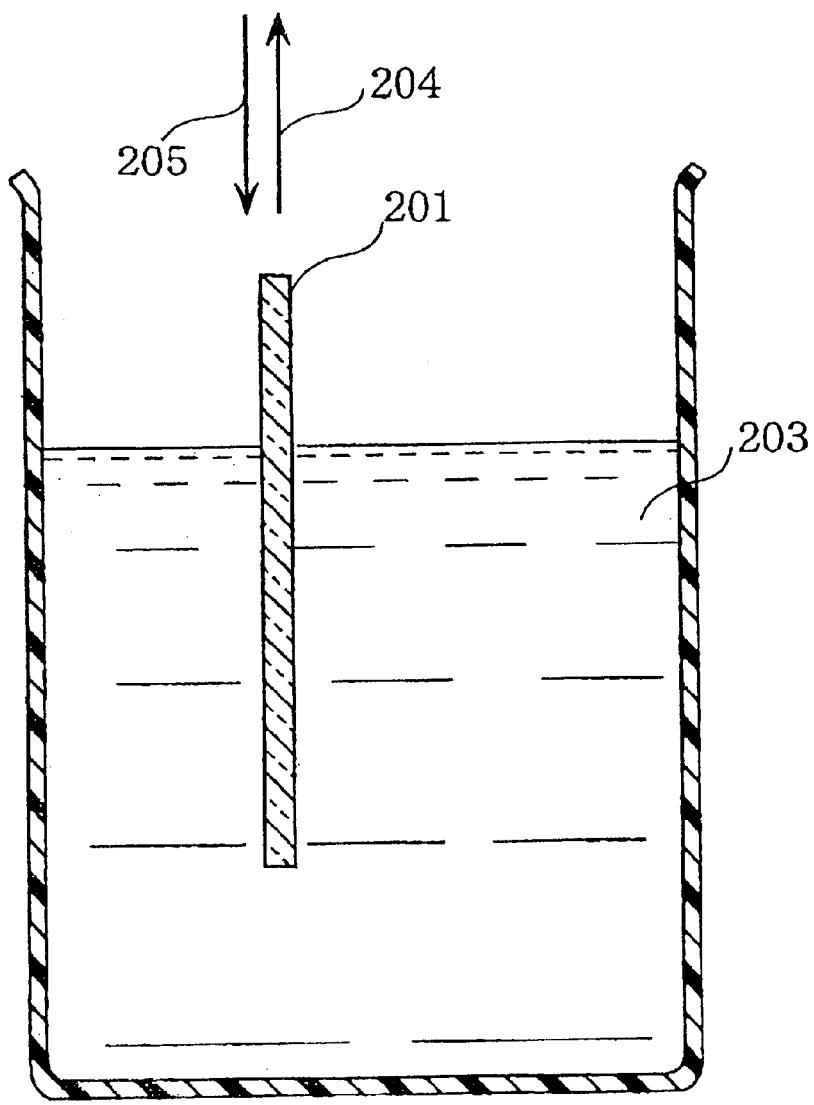

With reference to FIGS. 4 and 5, a method of preparing liquid crystal alignment films is detailed below. A glass substrate (which contains many hydroxyl groups) having a transparent electrode formed on the surface thereof was thoroughly washed and degreased. Thus, a glass substrate 201 was prepared. Meanwhile, a silane-based chemical adsorbate compound synthesized according to (1) above was dissolved into a mixed solvent of chloroform and a well-dehydrated siloxane-based solvent (KF96L available from Shin-Etsu Chemical Co., Ltd.) at a concentration of about 1 wt. %, Thus, a chemisorption solution 202 was prepared.

Subsequently, in the manner as shown in FIG. 4, the substrate 201 was soaked in the chemisorption solution 202 for about 1 hour under a dry atmosphere having a relative humidity of 30% or lower (Process A). Then, in the manner as shown in FIG. 5, the substrate 201 was repeatedly put into and taken out of chloroform 203 (aprotic solvent) to rinse the substrate surfaces (Process B). Thereafter, the substrate 201 was pulled up in the direction of the arrow 204 and left standing vertically under dry atmosphere to drain-dry the cleaning solution (Process C). Subsequently, the surfaces of the substrate 201 were exposed to air containing moisture (50–80% relative humidity) (Process D).

The above-described processes have the following chemical significance, In the process A in which the substrate 201 is soaked in the chemisorption solution 202, SiCl groups in the chlorosilane-based chemical adsorbate compound and hydroxyl groups on the surface of the substrate were dehydrochlorinated. By this process, the chlorosilane-based chemical adsorbate compound is firmly bonded to the surface of the substrate 201. In the process B in which the substrate 201 pulled out from the chemisorption solution 202 is rinsed with chloroform 203, unreacted chemical adsorbate compound is removed from the substrate surface. This process is necessary for forming a monomolecular thin film. In the drain-drying process (Process C) which follows the rinsing, adsorbed molecules are aligned in a certain direction. When the substrate with the cleaning solution remaining thereon is drain-dried by standing the substrate along a certain direction, the adsorbed molecules are pre-aligned along the drain-drying direction. It is noted that in the case where the substrate 201 is left standing vertically after pulled out from the cleaning solution as in FIG. 5, the drain-drying direction is the direction of the arrow 205. In the process D in which the substrate surface after drain-drying is exposed to air containing moisture, remaining Cl in SiCl groups are reacted with moisture in the air to be dehydrochlorinated. By this reaction, the adsorbed molecules are bonded each other by siloxane bonds.

By the above-described processes, a monomolecular film 209 (pre-aligned state) was formed in which the chlorosilane-based chemical adsorbate compound was bonded to hydroxyl groups on the substrate surface by siloxane bonds. The monomolecular film 209 comprises a monomolecular thin film composed of the chemical bonding unit represented by the chemical formula 206. It is noted that in place of soaking the substrate 201 in the chemisorption solution 202, a method of applying the chemisorption solution 202 onto the surface of the substrate 201 may be employed.

Chemical Formula 206

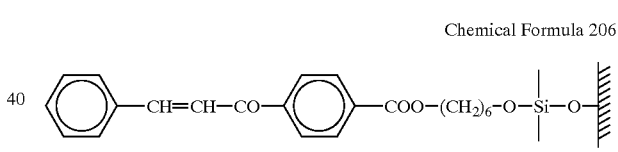

The film thickness of the monomolecular film 209 thus prepared was measured with the use of an euipsometer (the refractive index being 1.45). The film thickness was about 2.5 nm.

The alignment characteristic of the monomolecular film 209 was examined by using a test cell. The test cell was prepared in the following manner. Two substrates each having the monomolecular film 209 formed thereon were prepared, and the substrates were attached so that the films were on the insides of the cell, the drain-drying directions were antiparallel, and the gap between the substrates was about 12 μm. Then, the perimeter of the plates was sealed, and thereafter a nematic liquid crystal (ZLI4792 available from Merck & Co., Inc.) was filled into the gap. Then, polarizing plates were placed on both outward surfaces of the test cell, and a visible light was allowed to transmit from one side of the cell. The transmitted light coming out from the other side of the cell was observed to evaluate the alignment state of the liquid crystal molecules. Thus, it was confirmed that the liquid crystal molecules were aligned along the drain-drying direction.

Process of Polarized Light Irradiation

Figure 6:
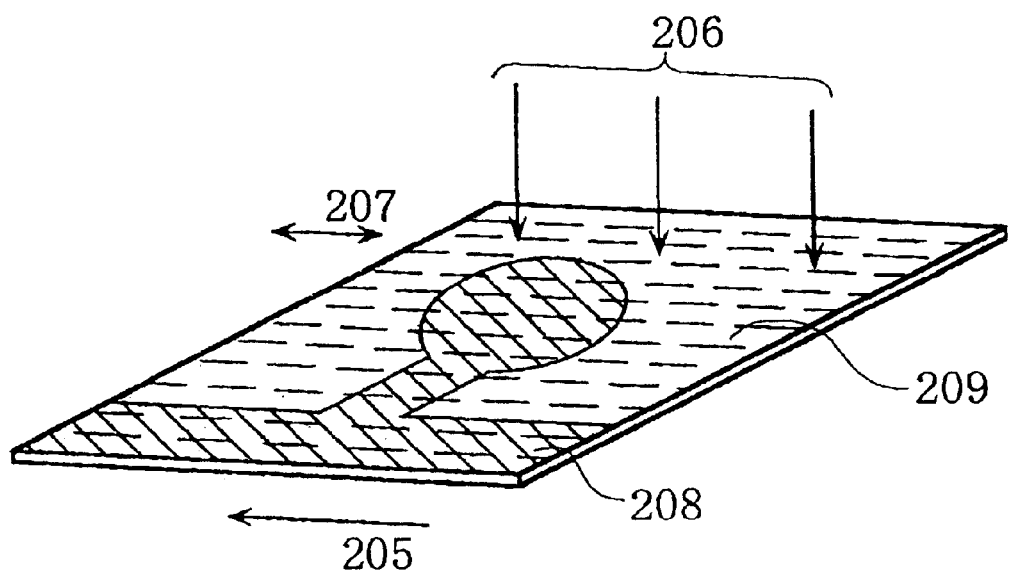
FIG. 6 schematically illustrates a rinsing step in the second group of the invention.

With reference to FIG. 6, a process of polarized light irradiation is detailed below. FIG. 6 shows a drain-drying direction 205, polarized ultraviolet light 206, a direction of polarization 207, a transparent electrode 208, and an aggregate of adsorbed molecules (monomolecular film) 209. A realignment treatment to the monomolecular film 209 was performed in the manner as shown in FIG. 6. Specifically, a Glan-Taylor polarizer is disposed so that the direction of polarization is substantially parallel to the drain-drying direction 205, and a 365 nm ultraviolet light 208 (2.1 mW/cm$^2$ after transmitting the polarizing film) was applied at 480 mJ with the use of a 500 W high pressure mercury lamp.

Subsequently, the monomolecular film irradiated with ultraviolet light 208 was analyzed by FT-IR (Fourier transform infrared spectroscopy) to study the chemical properties thereof. Thus, it was recognized that the monomolecular film showed a difference in IR absorption between the direction of polarization and the direction perpendicular thereto. Specifically, the IR absorption of the direction of polarization was noticeably decreased in comparison with that of the direction perpendicular thereto. The decrease of IR absorption indicates that the photosensitive groups (carbon-carbon double bonds) in the chalcone skeletons are crosslinked by receiving the light energy in the direction of polarization. Therefore, it was confirmed that applying polarized ultraviolet light was able to cause the crosslinking.

While the direction of the crosslink of adsorbed molecules was not fully discovered by the FT-IR analysis, it is evident that when the adsorbed molecules each other are crosslinked, the configuration of the adsorbed molecules each other becomes stable. Accordingly, it is considered that the monomolecular film (liquid crystal alignment film) subjected to the realignment treatment has a more stable alignment state than the foregoing pre-aligned film.

Using the substrate having a realigned liquid crystal alignment film formed thereon, a liquid crystal cell was prepared in the same manner as that of the foregoing test cell in order to evaluate the liquid crystal alignment characteristic. The result of the test showed that when no voltage was applied to the cell, a sufficient light transmission through the cell was observed, whereas a voltage of 3 V was applied, the light transmission was blocked. This indicates that the voltage application caused the change of the liquid crystal alignment from homogeneous alignment to homeotropic alignment. In addition, the pretilt angle was measured by an optical crystal rotation method. Consequently, it was shown that the pretilt angle was about 2°, and the liquid crystal molecules were aligned along the direction of polarization.

From the results above, it was confirmed that an ultra thin liquid crystal alignment film capable of achieving a high contrast ratio was realized by subjecting the aggregate of the adsorbed molecules each having a chemical bonding unit represented by the above chemical formula 206 to the realignment treatment involving crosslinking in addition to the pre-alignment treatment. Further, it was confirmed that the adsorbed molecules were crosslinked along a certain direction in the resultant liquid crystal alignment film. Therefore, the alignment control characteristic of the liquid crystal alignment film cannot be easily degraded. It is noted that the adsorbed molecules are crosslinked each other at carbon-carbon double bonds in the chalcone skeletons.

EXAMPLE 2-2

Figure 7:
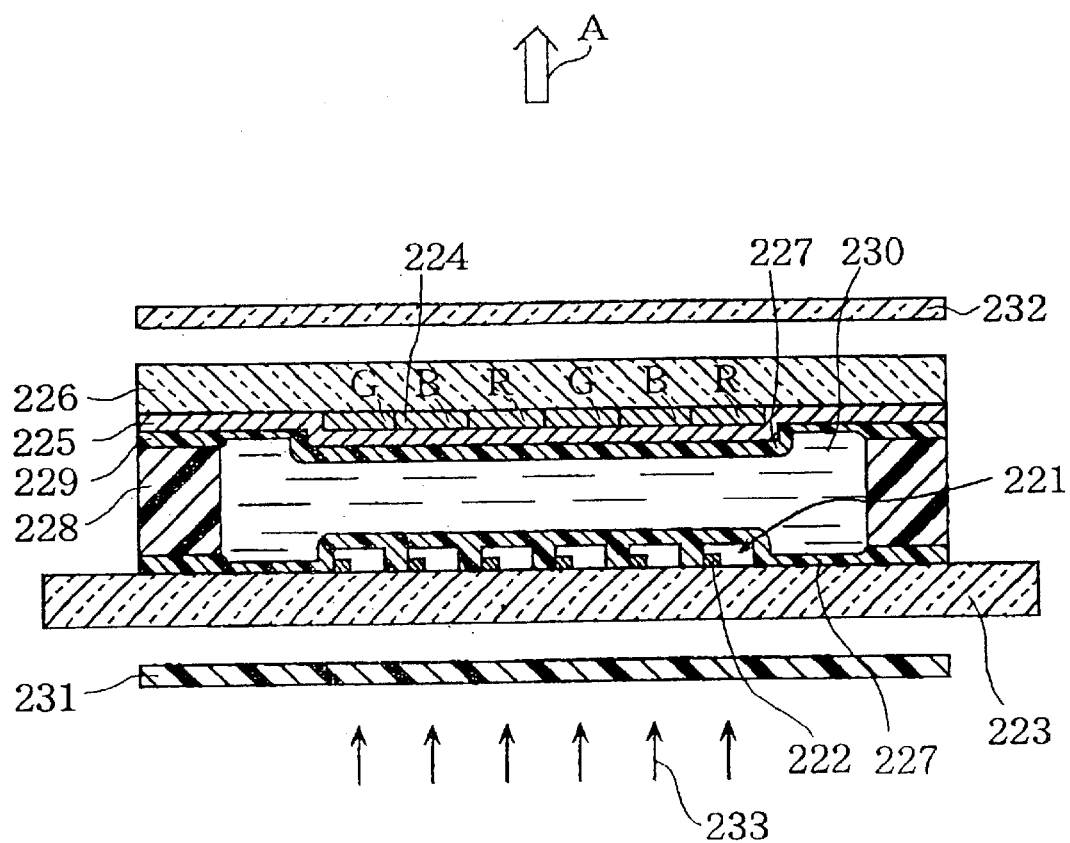
FIG. 7 is a schematic cross sectional view of a liquid crystal display device of Example 2-1 in the second group of the invention.

In Example 2-2, using a substrate on which pixel electrodes were arrayed in a matrix, a liquid crystal alignment film was formed in a manner analogous to that in the foregoing Example 2-1, and using the substrate having the liquid crystal alignment film formed thereon, a liquid crystal display device was produced. Referring now to FIG. 7, a producing process of a liquid crystal display device in accordance with Example 2-2 is described below.

As show in FIG. 7, a first substrate 223 comprises a group of first transparent electrodes 221 and a group of transistors 222 for driving the transparent electrodes, and a second substrate 226 comprises a group of color filters 224 and a second transparent electrode 225 (common electrode). A chemisorption solution prepared in the same manner as in Example 2-1 was contacted with the surfaces of the first substrate 223 and the second substrate 226. Thereafter, the drain-drying and irradiation with polarized light were performed in the same manner as in the foregoing Example 2-1. Thus, substrates 223 and 226 each having the liquid crystal alignment film thereon were prepared.

The alignment control characteristics of these substrates 223 and 226 were examined in the same manner as in the foregoing Example 2-1. Consequently, it was found that a liquid crystal alignment film 227 in which liquid crystal molecules were realigned along the electrode pattern was formed on each of the substrates. Then, the substrates 223 and 226 each having the liquid crystal alignment film were sandwiched so that the alignment directions of the alignment films were 90 degrees twisted and a 4.5 $\mu$m cell gap was formed with the use of spacer 228 and adhesive 229. Thus, a liquid crystal cell was formed.

Subsequently, a TN liquid crystal (ZLI4792 available from Merck & Co., Inc.) was filled into the cell gap, and the cell was hermetically sealed. Thereafter, the polarizing plates 231 and 232 were attached thereto. Thus, a liquid crystal display device was produced.

The pretilt angle of the liquid crystal in the above-described liquid crystal cell was 5°. It was confirmed that when the device was driven with video signals while a backlight 233 being applied, clear images were displayed in the direction indicated by the arrow A.

EXAMPLE 2-3

A multi-domain type liquid crystal alignment film in which four domains having different alignment directions are provided in each single pixel in a pattern-like manner was prepared in the following manner. After the pre-alignment treatment in the foregoing Example 2-2, the substrate with the liquid crystal alignment film was exposed one time to a polarized ultraviolet light while a mask such that each pixel is divided into four domains in a checkered pattern-like manner was being placed over the polarizing plate. Thereafter, a multi-domain type liquid crystal display device in accordance with Example 2-3 was produced in the same manner as in the foregoing Example 2-2 except that the above-described multi-domain type liquid crystal alignment film was employed.

The device thus produced was driven by video signals as in the same manner as in the foregoing Example 2-2. Thereby, it was confirmed that the device of Example 2-3 was capable of displaying images with wider viewing angles than those in the foregoing Example 2-2.

EXAMPLE 2-4

Two comb-shaped electrodes interdigitated each other are provided on the same surface on a substrate, and a realigned liquid crystal alignment film was formed on these comb-shaped electrodes in the same manner as in the foregoing Example 2-1. Thereafter, the substrate provided with the liquid crystal alignment film was sandwiched with a counter substrate, and liquid crystal cell was prepared in a usual manner. Thus, an in-plane witching (IPS) type liquid crystal display device was produced.

The IPS type liquid crystal display device thus produced was also subjected to an image display test using video signals in the same manner as in the foregoing Examples 2-2 and 2-3. Thereby, it was confirmed that the device in accordance with Example 2-4 was capable of displaying images with wide viewing angles.

Supplementary Remarks in the Second Group of the Invention (1) In the foregoing Examples 2-2 and 2-3, the liquid crystal alignment films were provided on both opposing substrate surfaces. However, the liquid crystal alignment film may be provided only one of the substrate surfaces. It is noted that when the liquid crystal alignment films in accordance with the present invention were provided on both opposing substrate surfaces, stability in alignment control is further increased.

(2) In the foregoing Examples 2-1 to 2-4, a 365 nm light by an ultra high pressure mercury lamp was employed as the polarized ultraviolet light. However, the polarized ultraviolet light is not limited thereto. Since the novel chemical adsorbate compound represented by the chemical formula 205 has a wide absorption range in the ultraviolet range as shown in FIG. 3, various ultraviolet lights can be employed. Examples of usable lights include ultraviolet lights having wavelengths of 436 nm, 405 nm, and 254 nm. A 248 nm ultraviolet light obtainable by KrF excimer laser may also be used.

(3) In the foregoing Example 2-3, the multi-domain type alignment film was prepared by exposing the substrate one time while placing such a patterned mask that each pixel is divided into four domains in a checkered pattern-like manner thereover. However, in place of this method, it is possible to employ a method in which the step of drain-drying and the step of applying polarized ultraviolet light are repeated. A specific example of such a method is given below.

When the step of drain-drying and the step of applying polarized ultraviolet light are repeated N-th time (N is an integer of 2 or greater), the drain-drying direction for the N-th time is made different from the drain-drying direction until the (N−1)-th time, and the substrate region to be irradiated with polarized ultraviolet light for the N-th time is made different from the substrate region irradiated until the (N−1)-th time. Thereby, the inclination of the long axes and/or the alignment direction of the molecules in the thin film with respect to the substrate surface plane can be varied in each of the divided domains in each pixel. It is also possible that the polarized ultraviolet light irradiation is performed a plurality of times while a region to be irradiated is made different each time. Nevertheless, the above-described method of repeating the step of drain-drying and the step of applying polarized ultraviolet light a plurality of times can easily control the direction of crosslinking, and therefore can obtain alignment films excellent in alignment control characteristic and alignment stability.

(4) In the foregoing Examples 2-1 to 2-4, chloroform, which contains no water, was used as the cleaning solution, but the cleaning solution is not limited thereto. Various solvents which contains no water and is capable of dissolving the chemical adsorbate compound may be employed. Examples of such solvents include, as aprotic solvents, chlorine-based solvents such as chlorine, aromatic solvents such as benzene and toluene, lactone-based solvents such as γ-butyrolactone, ester-based solvents such as ethyl acetate, and as protic solvents, alcohol-based solvents such as methanol and ethanol.

(5) For the liquid crystal display device according to the present invention, various types of liquid crystals may be employed, including nematic liquid crystals, smectic liquid crystals, discotic liquid crystals, and ferroelectric liquid crystals, etc. However, the liquid crystal alignment film of the present invention represented by the chemical formula 202 shows a strong alignment control effect particularly on twisted nematic (TN) type liquid crystals. Accordingly, the liquid crystal display device according to the present invention is preferable to be a 90° twisted nematic liquid crystal display device employing TN liquid crystals. Examples of the TN liquid crystals include biphenyl types, terphenyl types, azoxy type, Schiff base types, phenylcyclohexane types, biphenylcyclohexane types, ester types, pyrimidine types, dioxane types, bicyclooctane types, and cubane types.

(6) In the foregoing Examples 2-1 to 2-4, the aggregate of adsorbed molecules (thin film) was formed on the substrate by contacting the chemical adsorbate compound with the surface of the substrate already provided with an electrode. However, it is also possible that an underlayer (a layer of another substance) having hydrophilic groups is firstly provided on a surface of a substrate having an electrode formed thereon, and thereafter the chemical adsorbate compound is chemically bonded to the substrate surface via the underlayer. This method is particularly effective in the case where the substrate surface has few hydrophilic groups. Examples usable as the underlayer include layers having hydrophilic groups such as OH groups, COOH groups, $NH_2$ groups, NH groups and SH groups on their surfaces. Specifically, $SiO_2$ layer, $TiO_2$ layer, and the like can be employed.

As has been described above, according to the second group of the invention, it is made possible to provide a remarkably thin and uniform liquid crystal alignment film free from alignment defects in comparison with conventional organic polymer-based liquid crystal alignment films. In the liquid crystal alignment film according to the invention, the adsorbed molecules are firmly bonded and fixed onto the electrode surface by chemical adsorption, and the adsorbed molecules are crosslinked with each other. Therefore, the liquid crystal alignment film according to the invention is excellent in adherence to the substrate, and moreover, the alignment control characteristics thereof do not degrade by external factors such as heat and friction. Furthermore, since every individual adsorbed molecule in the film takes part in controlling the alignment of liquid crystal molecules, remarkably good alignment control characteristics are achieved.

In addition, such a liquid crystal alignment film is a monomolecular thin film composed of an aggregate of the adsorbed molecules, and has an extremely small thickness. Therefore, the alignment film exhibits a remarkably desirable property as a liquid crystal alignment film that it does not obstruct light transmission, nor disturb the electric field driving the liquid crystal since the electrical resistivity is small.

Further, according to a producing method of the present invention, multi-domain type liquid crystal alignment films in which alignment directions differ in each of the domains divided in a pattern-like manner can be produced in a relatively simple manner. By employing such liquid crystal alignment films according to the invention, it is made possible to realize, without increasing cost, homeotropic alignment mode liquid crystal display devices of multi-domain type which can achieve wide viewing angles, high quality pictures, and high contrast ratios as well as high speed responses.

Preferred Embodiments in the Third Group

EXAMPLE 3-1

A method of synthesizing a novel chemical adsorbate compound in accordance with the invention is described by the following three reaction steps. The synthesized chemical adsorbate compound (silane-based chemical adsorbate compound) comprises a chalcone skeleton group, a linear hydrocarbon group $(CH_2)_6$ ether-linked at the 4 position of the benzene ring in the chalcone skeleton group, and an $SiCl_3$ group ether-linked to the hydrocarbon group. This chemical adsorbate compound is represented by the chemical formula 305 above.

Reaction Step 1

A 10 L reaction flask was charged with 200 g (1.64 mole) of 4-hydroxybenzaldehyde, 196.8 g (1.64 mole) of acetophenone, and 1.8 L of ethanol. Then, the temperature of the solution was reduced to 5° C. or lower, and 3.3 L of 10 wt. % aqueous solution of sodium hydroxide was dripped into the mixture over a period of 2.5 hours. Thereafter, the solution was warmed to room temperature and stirred for 3 days to react.

Figure 8:
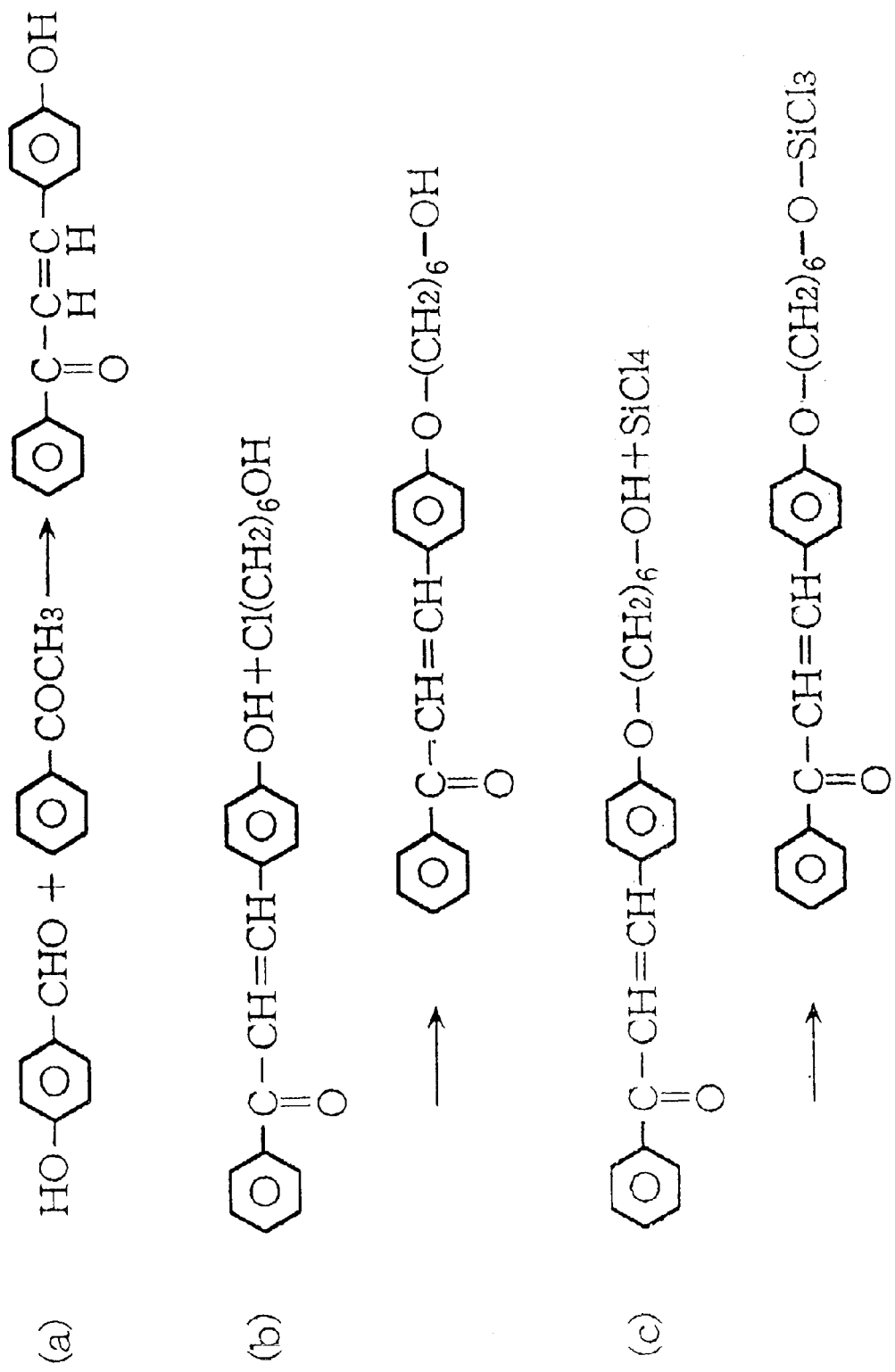
FIG. 8 shows a synthesis reaction formula of a chemical adsorbate in accordance with the third group of the invention.

The reaction solution was poured into 5 L of ice water, and then 6.5 L of 1N hydrochloric acid was added thereto. Thereafter, the solution was extracted with ethyl acetate. Then, the ethyl acetate extract solution was rinsed with saturated salt solution and dehydrated with anhydrous magnesium sulfate, and the solvent was removed by distilling to obtain a solid material. The resultant solid material was rinsed with chloroform and then dried, and thus 73.8 g of purified product was obtained. FIG. 8(a) shows the reaction formula of this reaction. The yield in this reaction was 20.1%.

Reaction Step 2

Under argon current, a 3 L reaction flask was charged with 4-hydroxychalcone 73.8 g (0.329 mole) and 1 L of dry DMF and ice-cooled, and 13.2 g (0.329 mole) of 60 wt. % aqueous solution of sodium hydride was added thereto over a period of 25 minutes. Thereafter, the reaction solution was warmed to room temperature, and stirred for 2 hours.

Also at room temperature, 45 g (0.329 mole) of 6-chlorohexanol was dripped into the reaction solution over a period of 30 minutes, and then, the reaction solution was heated to 80° C. and allowed to react for 4 hours. Thereafter, the reaction solution was poured into ice water and subjected to extraction with ethyl acetate. The extract solution was rinsed with water and dehydrated with magnesium sulfate, and the solvent was removed by distilling to obtain crude crystals.

The crude crystals were recrystallized with the use of hexane/ethyl acetate=5/3 (volume ratio), and thus 70 g of purified product was obtained. FIG. 8(b) shows the reaction formula of this reaction. The yield in this reaction was 65.6%. The purity of the purified product was 98% according to high-performance liquid chromatography.

Reaction Step 8

Under argon current, a 500 ml reaction flask was charged with 60 g (0.185 mole) of 4-(6-hydroxyhexyl)chalcone and 240 g (1.4 mole) of silicon tetrachloride, and the mixture was stirred at room temperature for 2 hours to cause reaction. Thereafter, excessive silicon tetrachloride was removed by distilling. Thus, 80 g of final product was obtained. FIG. 8(c) shows the reaction formula of this reaction.

Figure 9:
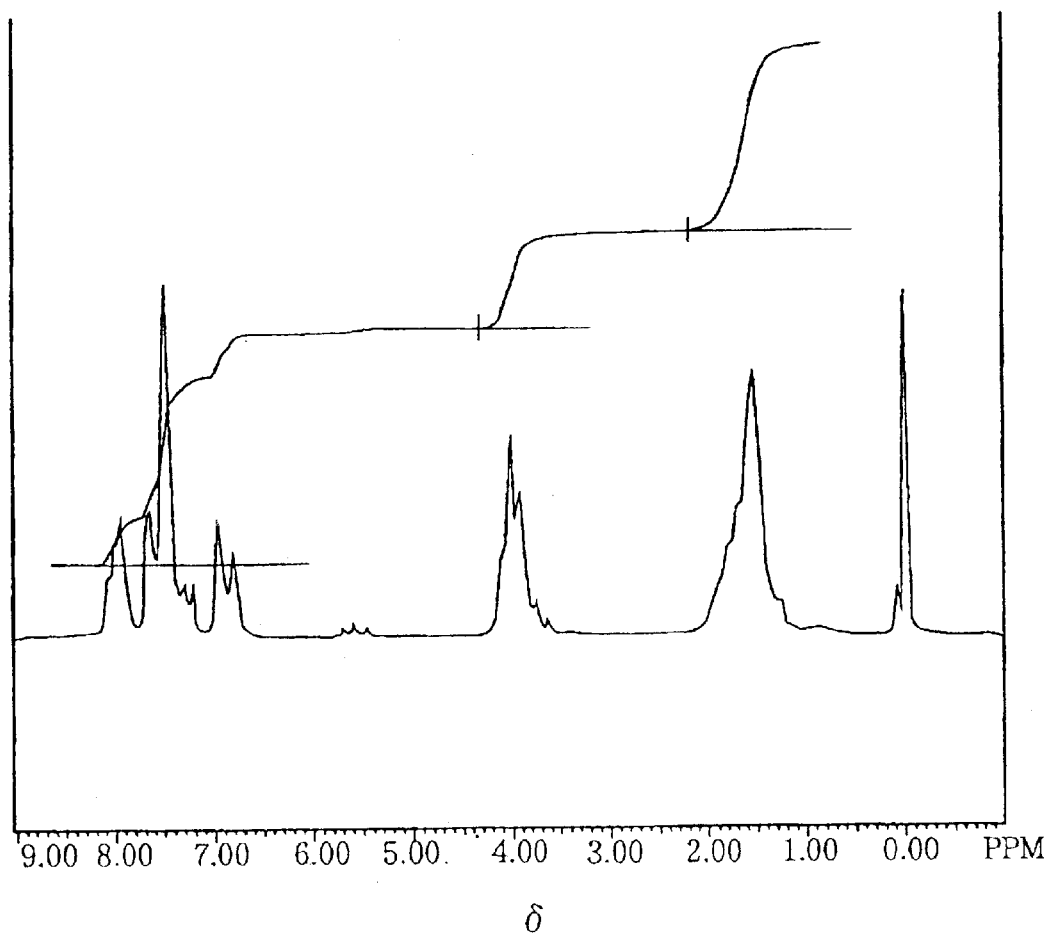
FIG. 9 is a $^1$H-NMR spectrum chart of the final product synthesized in accordance with the synthesis reaction formula in FIG. 8.

Each of the above-described products was analyzed by measuring infrared absorption spectra, MS spectra, and $^1$H-NMR spectra. The analyses confirmed that in each of the reaction steps, the intended compounds were obtained. In FIG. 9 illustrating the $^1$H-NMR spectrum of the final product, the peaks shown in the figure demonstrate that the final product has the chemical structure represented by the foregoing chemical formula 305.

Figure 10:
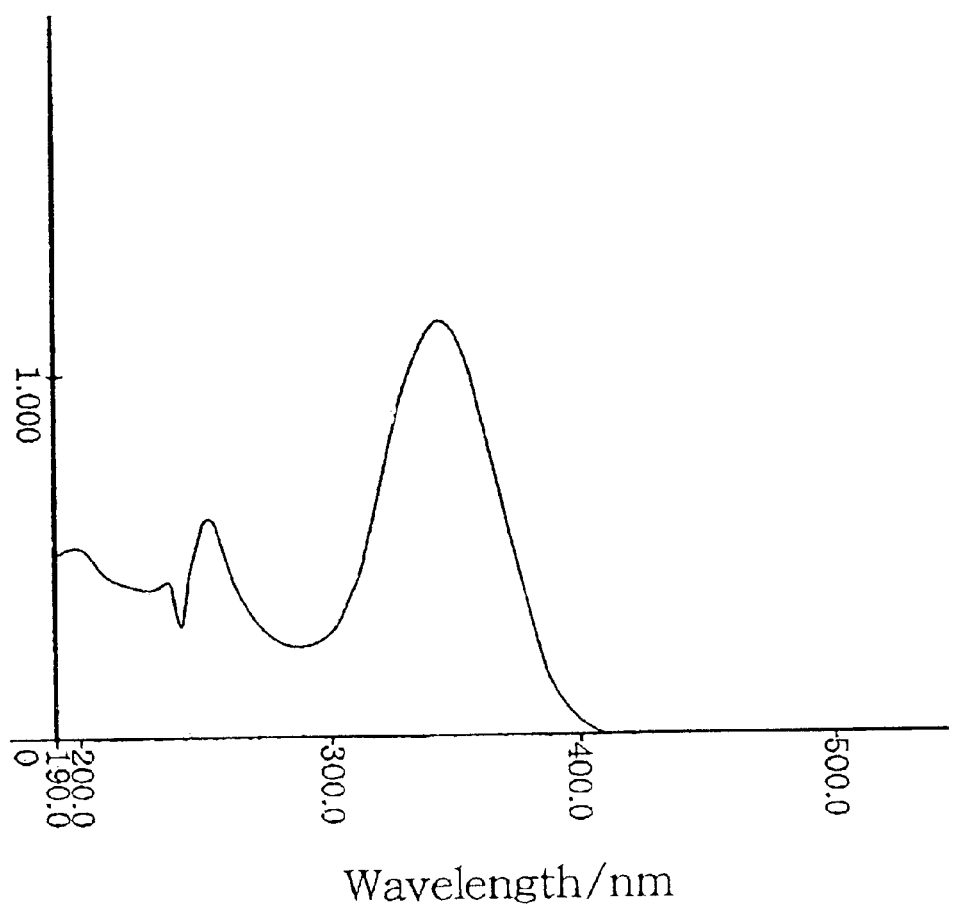
FIG. 10 is an ultraviolet-visible absorption spectrum chart of the final product synthesized in accordance with the synthesis reaction formula in FIG. 8.

Further, the final product was dissolved in chloroform, and ultraviolet-visible absorption spectrum was measured. The result is shown in FIG. 10. FIG. 10 shows that the final product has the maximum absorption peak at 344 nm in the ultraviolet range, but has no absorption peak in the visible range. This confirms that the above-described chlorosilane-based chemical adsorbate compound has low sensitivity to visible light, but has high sensitivity to 344 nm ultraviolet light.

It is noted that, the $^1$H-NMR spectroscopy was performed with the use of R-1200 manufactured by Hitachi, Ltd., the IR spectroscopy with FTIR4300 manufactured by Shimadzu, Corp., and the UV-VIS spectroscopy with UV-240 also manufactured by Shimadzu, Corp.

It is to be noted that while a synthesizing method of a specific compound represented by chemical formula 305 is described here, the chemical adsorbate compound represented by the foregoing general formula (chemical formula 301) can be synthesized by using HO—$(CH_2)_n$—OH (n=1 to 20) in place of HO—$(CH_2)_6$—OH in the reaction of FIG. 8(c), and using $SiX_4$ (where X is halogen) in place of $SiCl_4$ in the reaction of FIG. 8(d).

The above-described compound has an ultraviolet light absorption peak in the long wavelength range near the visible light range, and such a chemical adsorbate compound is desirable in the crosslinking reaction of the compound. This is because crosslinking reaction of such a compound can be performed by using conventional ultraviolet lamps having an absorption peak at 365 nm, and therefore, no special apparatus for the crosslinking reaction is required. Moreover, ultraviolet irradiation with a long wavelength ultraviolet light tends not to cause side reactions (decomposition) in the crosslinking reaction. Therefore, good films can be formed.

Film Formation Test

Using the above-described chemical adsorbate compound, a film was formed on a glass substrate. Film-forming performance of the chemical adsorbate compound and characteristics of the formed film were thereby tested. The method of forming the film was as follows. The above-described chemical adsorbate compound was dissolved in a 1/9 mixed solvent of xylene/silicone (KF96L available from Shin-Etsu Chemical Co., Ltd.) to have a concentration of 0.5 wt. %, and into the resulting solution, a glass substrate was soaked for about 2 hours. Thereafter, the substrate was taken out of the solution, and the surfaces of the substrate were sufficiently rinsed with chloroform in such a state that the surface plane of the substrate was inclined. Then, the substrate was dried in the air having a moderate humidity (40% or higher) while being maintained in the inclined state.

The contact angle of the film with water was measured. The contact angle was 81 degrees, which showed that the thin film had sufficient water repellency. In addition, the film thickness of the thin film was measured with the use of an ellipsometer (the refractive index being 1.45). The film thickness was found to be about 2.5 nm, which showed that a substantially monomolecular thin film was formed.

Polarized Light Irradiation and Liquid Crystal Alignment Control Characteristic

The thin film produced according to the above-described manner was irradiated with a polarized light (365 nm wavelength, 2.5 mW/cm$^2$ light intensity) produced by using a polarizing plate. The irradiated thin film was then examined by UV-VIS spectroscopy. As a result, it was confirmed that an absorption peak at 344 nm almost disappeared, and the molecules were crosslinked by the polarized light irradiation at the position of carbon-carbon double bond (—CH=CH—) in the foregoing chemical formula 305.

Meanwhile, a liquid crystal cell was prepared in the following manner. The thin film irradiated with polarized light was formed on a substrate, and the substrate with the thin film was attached to another glass plate so that the thin film was on the inside of the cell and a gap of about 12 μm was provided between the substrate and the glass plate. Then, the perimeter of the plates was sealed, and thereafter a nematic liquid crystal (ZLI4792 available from Merck & Co., Inc.) was filled into the gap. Thus, a test cell was prepared. Polarizing plates were placed on both outward surfaces of the test cell, and a liquid crystal alignment control characteristic of the thin film was examined using visible light. As a result, it was confirmed that the liquid crystal molecules in the test cell were uniformly aligned in the direction of the polarized light In addition, a substrate having the thin film irradiated with polarized light was heated at about 200° C. for 1 hour, and using the substrate, a test cell was prepared in the same manner as described above to examine alignment directions of the liquid crystal molecules. As a result, it was confirmed that the above-described chemical adsorbate compound was capable of forming a thermally stable alignment film.

It is noted that the alignment state of liquid crystal can be confirmed by allowing to transmit a light from one side of the liquid crystal cell on which a polarizing plate is disposed and observing the transmitted light coming out from the other side of the cell.

As understood from the above description, the novel chemical adsorbate compound in accordance with the third group of the invention has a functional group that can be firmly chemically bonded to a hydrophilic group on a surface of a substrate material, and a photosensitive group sensitive to an ultraviolet light at about 844 nm. The chemical adsorbate compound is colorless and stable to visible light.

By employing the chemical adsorbate compound, a monomolecular thin film composed of an aggregate of adsorbed molecules can be easily formed on a substrate material surface, and further, by applying ultraviolet light to the thin film, a functional film in which adsorbed molecules are crosslinked with each other in a certain direction can be formed. The thin film so formed exhibits many advantages such as excellent transparency, water repellency, chemical stability, adhesiveness to substrate materials, and durability. Furthermore, the thin film can serve as a non-rubbed liquid crystal alignment film capable of aligning liquid crystal molecules in a certain direction.

Hence, the chemical adsorbate compound in accordance with the third group of the invention is useful as a material for modifying a substrate material surface as well as a material for liquid crystal alignment films.

Preferred Embodiments in the Fourth Group

EXAMPLE 4-1

A liquid crystal alignment film in accordance with Example 4-1 is described below.
(1) Synthesis of Chemical Adsorbate Compound A compound comprising a chalcone skeleton group, a linear hydrocarbon group $(CH_2)_6$ ether-linked at the 4 position of the benzene ring in the chalcone skeleton group, and an $SiCl_3$ group ether-linked to the hydrocarbon group, which compound is represented by the following chemical formula 405, was synthesized in the same manner as in the foregoing Example 3-1, and employed as a chemical adsorbate compound.

Chemical Formula 405

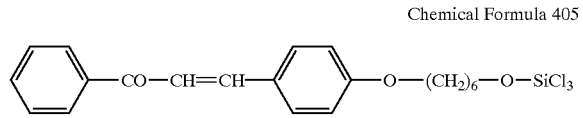

It is to be understood that chemical adsorbate compounds usable for the liquid crystal alignment film of the fourth group of the invention are not limited to the compound represented by the previously-described chemical formula 404. For example, other divalent functional groups may be employed in place of $(CH_2)_n$ in the foregoing chemical formula 404. Examples of such divalent functional groups include a divalent functional group containing a carbon-carbon double bond or a carbon-carbon triple bond in part of the hydrocarbon groups, or a divalent functional group in which hydrogen in the hydrocarbon groups is substituted by other functional groups (e.g., methyl groups, methyl halide groups, hydroxyl groups, cyano groups, or the like) and/or atoms (e.g., F, Cl, Br, I, or the like), and a divalent functional group in which a C—O—C (ether) bond or a C—CO—C— (carbonyl) bond is substituted for a C—C bond in the hydrocarbon group.

(2) Preparation of Liquid Crystal Alignment Film

Figure 11:
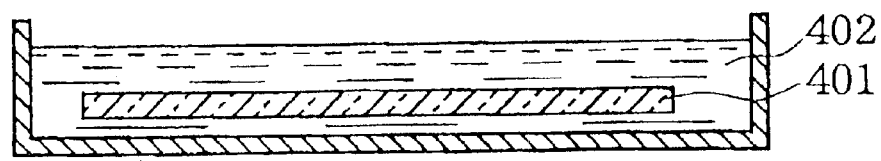
FIG. 11 schematically illustrates a chemisorption step in the fourth group of the invention.
Figure 12:
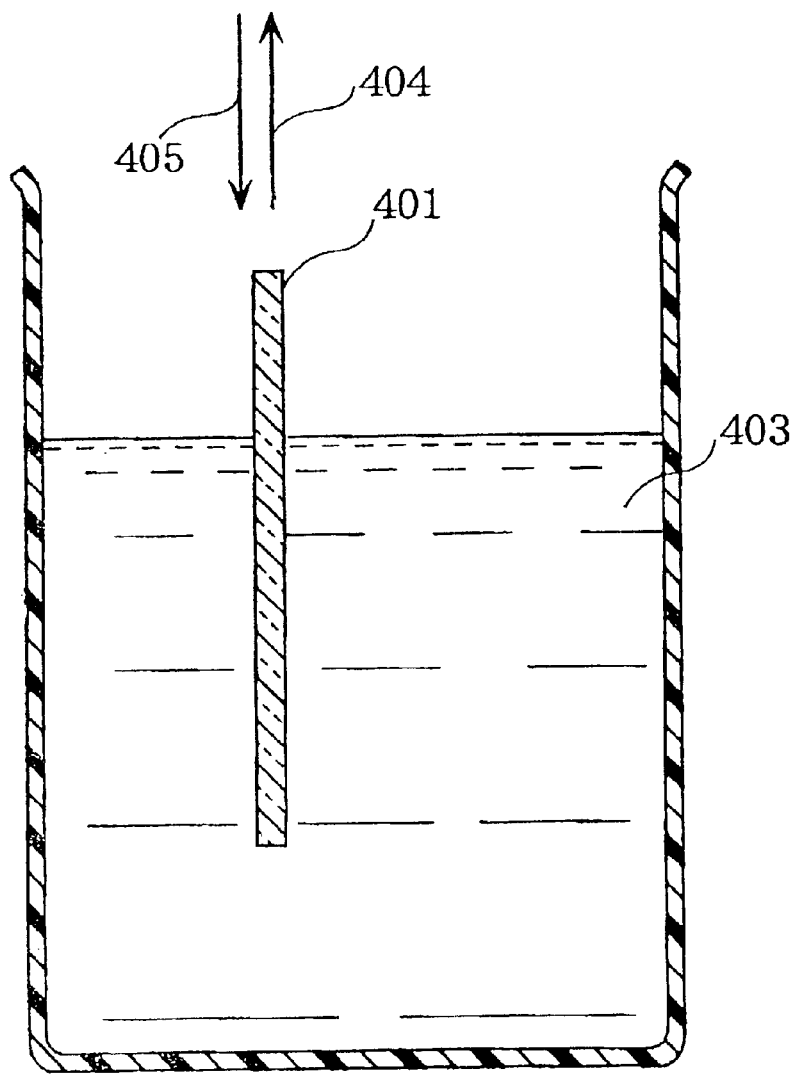
FIG. 12 schematically illustrates a rinsing step in the fourth group of the invention.

With reference to FIGS. 11 and 12, a method of preparing liquid crystal alignment films is detailed below. A glass substrate (which contains many hydroxyl groups) having a transparent electrode formed on the surface thereof was thoroughly washed and degreased. Thus, a glass substrate 401 was prepared. Meanwhile, a silane-based chemical adsorbate compound synthesized according to (1) above was dissolved into a mixed solvent of chloroform and a well-dehydrated siloxane-based solvent (KF96L available from Shin-Etsu Chemical Co., Ltd.) at a concentration of about 1 wt. %. Thus, a chemisorption solution 402 was prepared.

Subsequently, in the manner as shown in FIG. 11, the substrate 401 was soaked in the chemisorption solution 402 for about 1 hour under a dry atmosphere having a relative humidity of 30% or lower (Process A). Then, in the manner as shown in FIG. 12, the substrate 401 was repeatedly put into and taken out of well-dehydrated chloroform 403 (aprotic solvent) to rinse the substrate surfaces (Process B). Thereafter, the substrate 401 was pulled up in the direction of the arrow 404 and left standing vertically under dry atmosphere to drain-dry the cleaning solution (Process C). Subsequently, the surfaces of the substrate 401 were exposed to air containing moisture (50–80% relative humidity) (Process D).

The above-described processes have the following chemical significance. In the process A in which the substrate 401 is soaked in the chemisorption solution 402, SiCl groups in the chlorosilane-based chemical adsorbate compound and hydroxyl groups on the surface of the substrate were dehydrochlorinated. By this process, the chlorosilane-based chemical adsorbate compound is firmly bonded to the surface of the substrate 401. In the process B in which the substrate 401 pulled out from the chemisorption solution 402 is rinsed with chloroform 403, unreacted chemical adsorbate compound is removed from the substrate surface. This process is necessary for forming a monomolecular thin film. In the drain-drying process (Process C) which follows the rinsing, adsorbed molecules are aligned in a certain direction. When the substrate with the cleaning solution remaining thereon is drain-dried by standing the substrate along a certain direction, the adsorbed molecules are pre-aligned along the drain-drying direction. It is noted that in the case where the substrate 401 is left standing vertically after pulled out from the cleaning solution as in FIG. 12, the drain-drying direction is the direction of the arrow 405. In the process D in which the substrate surface after drain-drying is exposed to air containing moisture, remaining Cl in SiCl groups are reacted with moisture in the air to be dehydrochlorinated. By this reaction, the adsorbed molecules are bonded each other by siloxane bonds.

By the above-described processes, a monomolecular film 409 (pre-aligned state) was formed in which the chlorosilane-based chemical adsorbate compound was bonded to hydroxyl groups on the substrate surface by siloxane bonds. The monomolecular film 409 comprises a monomolecular thin film composed of the chemical bonding unit represented by the chemical formula 406. It is noted that in place of soaking the substrate 401 in the chemisorption solution 402, a method of applying the chemisorption solution 402 onto the surface of the substrate 401 may be employed.

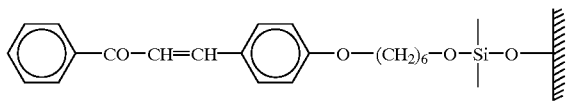

The film thickness of the monomolecular film 409 thus prepared was measured with the use of an ellipsometer (the refractive index being 1.45). The film thickness was about 2.5 nm.

The alignment characteristic of the monomolecular film 409 was examined using a test cell. The test cell was prepared in the following manner. Two substrates each having the monomol ocular film 409 formed thereon were prepared, and the substrates were attached so that the films were on the insides of the cell, the drain-drying directions were antiparallel, and the gap between the substrates was about 12 $\mu$m. Then, the perimeter of the plates was sealed, and thereafter a nematic liquid crystal (ZLI4792 available from Merck & Co., Inc.) was filled into the gap. Then, polarizing plates were placed on both outward surfaces of the test cell, and a visible light was allowed to transmit from one side of the cell, The transmitted light coming out from the other side of the cell was observed to evaluate the alignment state of the liquid crystal molecules. Thus, it was confirmed that the liquid crystal molecules were aligned along the drain-drying direction.

Process of Polarized Light Irradiation

Figure 13:
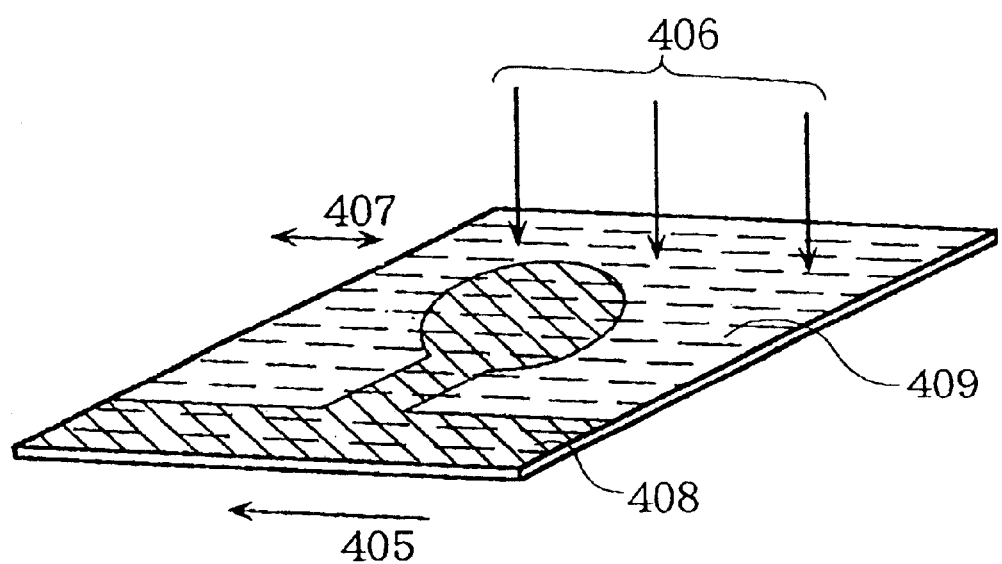
FIG. 13 schematically illustrates a step of applying a polarized ultraviolet light in the fourth group of the invention.

Referring to FIG. 13, detailed below is a process of polarized light irradiation, which is a step of realigning the monomolecular film 409. FIG. 13 shows a drain-drying direction 405, polarized ultraviolet light 406, a direction of polarization 407, a transparent electrode 408, and an aggregate of adsorbed molecules (monomolecular film) 409. As shown in FIG. 13, a Glan-Taylor polarizer is disposed so that the direction of polarization 407 is substantially parallel to the drain-drying direction 405, and a 365 nm ultraviolet light 408 (2.1 mW/cm$^2$ after transmitting the polarizing film) was applied at 480 mJ with the use of a 500 W high pressure mercury lamp.

Subsequently, the monomolecular film irradiated with ultraviolet light 408 was analyzed by FT-IR (Fourier transform infrared spectroscopy) to study the chemical properties thereof Thus, it was recognized that the monomolecular film showed a difference in IR absorption between the direction of polarization and the direction perpendicular thereto. Specifically, the IR absorption of the direction of polarization was noticeably decreased in comparison with that of the direction perpendicular thereto. The decrease of IR absorption indicates that the photosensitive group in the chalcone skeleton (carbon-carbon double bond) is crosslinked by receiving light energy in the direction of polarization. Hence, it was confirmed that applying polarized ultraviolet light was able to cause crosslinking.

The direction of the crosslink of adsorbed molecules was not fully discovered from the result of the FT-IR spectroscopy. However, it is evident that the adsorbed molecules were crosslinked with each other. Thereby, the configuration of the adsorbed molecules each other becomes stable. In other words, the monomolecular film (liquid crystal alignment film) subjected to the realignment treatment has a more stable alignment state than the foregoing pre-aligned film.

Using the substrate having a realigned liquid crystal alignment film formed thereon, a liquid crystal cell was prepared in the same manner as that of the foregoing test cell in order to evaluate the liquid crystal alignment characteristic. The result of the test showed that when no voltage was applied to the cell, a sufficient light transmission through the cell was observed, whereas a voltage of 3 V was applied, the light transmission was blocked. This indicates that the voltage application caused the change of the liquid crystal alignment from homogeneous alignment to homeotropic alignment. In addition, the pretilt angle was measured by an optical crystal rotation method. Consequently, it was shown that the pretilt angle was about 2°, and the liquid crystal molecules were aligned along the direction of polarization.

In addition, a substrate having a thin film irradiated with the polarized light formed on its surface was heated at about 200° C. for 1 hour, and using the substrate, a test cell was prepared in the same manner as described above to examine the alignment directions of the liquid crystal molecules. The result confirmed that the realigned liquid crystal alignment film was thermally stable.

From the results above, it was confirmed that when the aggregate of the adsorbed molecules each having a chemical bonding unit represented by the above chemical formula 406 was subjected to the realignment treatment involving crosslinking in addition to the pre-alignment treatment, the adsorbed molecules in the resultant liquid crystal alignment film were crosslinked with each other in a certain direction. It was also confirmed that the resultant alignment film was stable against external detrimental factors, such as heat, and had a high contrast ratio. It is noted that the adsorbed molecules are crosslinked with each other at carbon-carbon double bonds in the chalcone skeletons.

EXAMPLE 4-2

Figure 14:
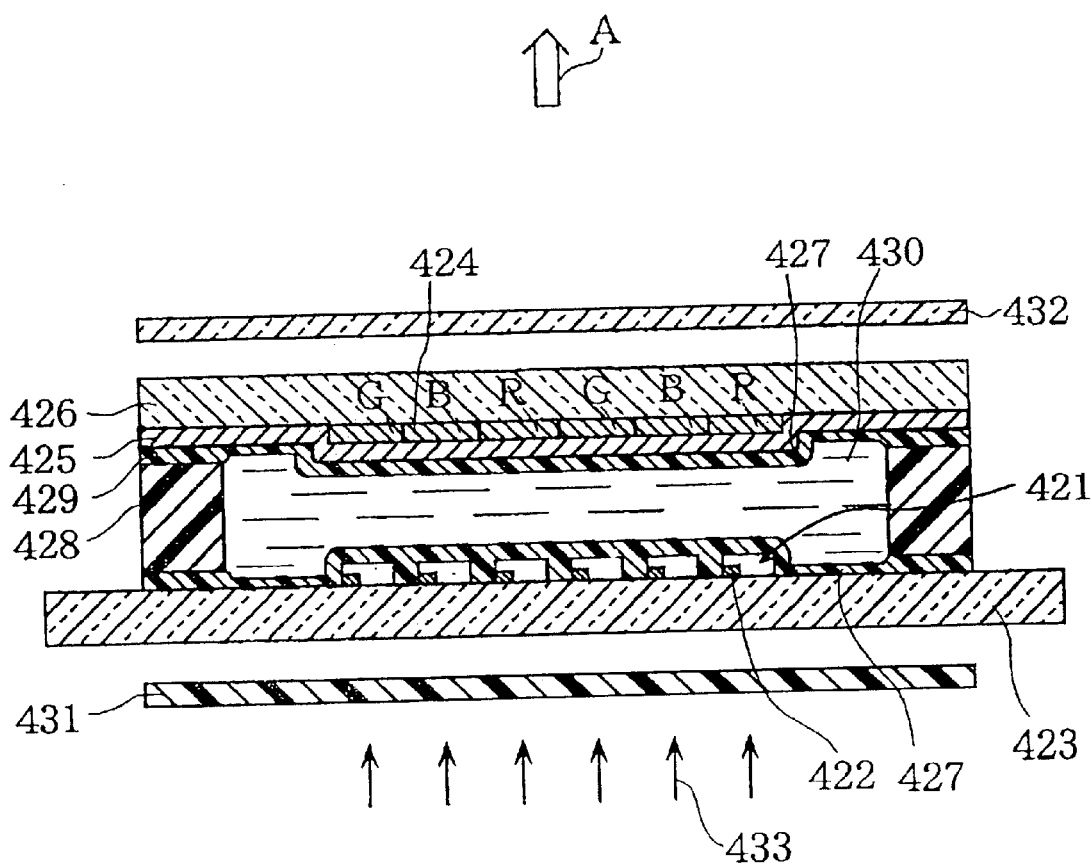
FIG. 14 is a schematic cross sectional view of a liquid crystal display device of Example 4-2 in the fourth group of the invention.

In Example 4-2, using a substrate on which pixel electrodes were arrayed in a matrix, a liquid crystal alignment film was formed in a manner analogous to that in the foregoing Example 4-1, and using the substrate having the liquid crystal alignment film formed thereon, a liquid crystal display device was produced. Referring now to FIG. 14, a producing process of a liquid crystal display device in accordance with Example 4-2 is described below.

As show in FIG. 14, a first substrate 423 comprises a group of first transparent electrodes 421 and a group of transistors 422 for driving the transparent electrodes, and a second substrate 426 comprises a group of color filters 424 and a second transparent electrode 425 (common electrode). A chemisorption solution prepared in the same manner as in Example 4-1 was contacted with the surfaces of the first substrate 423 and the second substrate 426. Thereafter, the drain-drying and irradiation with polarized light were performed in the same manner as in the foregoing Example 4-1. Thus, substrates 423 and 426 each having the liquid crystal alignment film thereon were prepared.

The alignment control characteristics of these substrates 423 and 426 were examined in the same manner as in the foregoing Example 4-1. Consequently, it was found that a liquid crystal alignment film 427 in which liquid crystal molecules were realigned along the electrode pattern was formed on each of the substrates. Then, the substrates 423 and 426 each having the liquid crystal alignment film were sandwiched so that the alignment directions of the alignment films were 90 degrees twisted and a 4.5 μm cell gap was formed with the use of spacer 428 and adhesive 429. Thus, a liquid crystal cell was formed.

Subsequently, a TN liquid crystal (ZLI4792 available from Merck & Co., Inc.) was filled into the cell gap, and the cell was hermetically sealed. Thereafter, the polarizing plates 431 and 432 were attached thereto. Thus, a liquid crystal display device was produced.

The pretilt angle of the liquid crystal in the above-described liquid crystal cell was 5°. It was confirmed that when the device was driven with video signals while a backlight 433 being applied, clear images were displayed in the direction indicated by the arrow A.

EXAMPLE 4-3

A multi-domain type liquid crystal alignment film in which four domains having different alignment directions are provided in each single pixel in a pattern-like manner was prepared in the following manner. After the pre-alignment treatment in the foregoing Example 4-2, the substrate with the liquid crystal alignment film was exposed one time to a polarized ultraviolet light while a mask such that each pixel is divided into four domains in a checkered pattern-like manner was being placed over the polarizing plate. Thereafter, a multi-domain type liquid crystal display device in accordance with Example 4-3 was produced in the same manner as in the foregoing Example 4-2 except that the above-described multi-domain type liquid crystal alignment film was employed.

The device thus produced was driven by video signals as in the same manner as in the foregoing Example 4-2. Thereby, it was confirmed that the device of Example 4-3 was capable of displaying images with wider viewing angles than those in the foregoing Example 4-2.

EXAMPLE 4-4

Two comb-shaped electrodes interdigitated each other are provided on the same surface on a substrate, and a realigned liquid crystal alignment film was formed on these comb-shaped electrodes in the same manner as in the foregoing Example 4-1. Thereafter, the substrate provided with the liquid crystal alignment film was sandwiched with a counter substrate, and a liquid crystal cell was prepared in a usual manner. Thus, an in-plane switching (IPS) type liquid crystal display device was produced.

The IPS type liquid crystal display device thus produced was also subjected to an image display test using video signals in the same manner as in the foregoing Examples 4-2 and 4-3. Thereby, it was confirmed that the device in accordance with Example 4-4 was capable of displaying images with wide viewing angles.

Supplementary Remarks in the Fourth Group of the Invention (1) In the foregoing Examples 4-2 and 4-3, the liquid crystal alignment films were provided on both opposing substrate surfaces. However, the liquid crystal alignment film may be provided only one of the substrate surfaces. It is noted that when the liquid crystal alignment films in accordance with the present invention were provided on both opposing substrate surfaces, stability in alignment control is further increased.

(2) In the foregoing Examples 4-1 to 4-4, a 365 nm light by an ultra high pressure mercury lamp was employed as the polarized ultraviolet light. However, the polarized ultraviolet light is not limited thereto. Since the novel chemical adsorbate compounds represented by the chemical formula 405 and so forth have a wide absorption range in the ultraviolet range as shown in FIG. 10, various ultraviolet lights can be employed. Examples of usable lights include ultraviolet lights having wavelengths of 436 nm, 405 nm, and 254 nm. A 248 nm ultraviolet light obtainable by KrF excimer laser may also be used.

(3) In the foregoing Example 4-3, the multi-domain type alignment film was prepared by exposing the substrate one time while placing such a patterned mask that each pixel is divided into four domains in a checkered pattern-like manner thereover. However, in place of this method, it is possible to employ a method in which the step of drain-drying and the step of applying polarized ultraviolet light are repeated. A specific example of such a method is given below.

When the step of drain-drying and the step of applying polarized ultraviolet light are repeated the N-th time (N is an integer of 2 or greater), the drain-drying direction for the N-th time is made different from the drain-drying direction until the (N−1)-th time, and the substrate region to be irradiated with polarized ultraviolet light for the N-th time is made different from the substrate region irradiated until the (N−1)-th time. Thereby, the inclination of the long axes and/or the alignment direction of the molecules in the thin film with respect to the substrate surface plane can be varied in each of the divided domains in each pixel. It is also possible that the polarized ultraviolet light irradiation is performed a plurality of times while a region to be irradiated is made different each time. Nevertheless, the above-described method of repeating the step of drain-drying and the step of applying polarized ultraviolet light a plurality of times can easily control the direction of crosslinking, and therefore can obtain alignment films excellent in alignment control characteristic and alignment stability.

(4) In the foregoing Examples 4-1 to 4-4, chloroform, which contains no water, was used as the cleaning solution, but the cleaning solution is not limited thereto. Various solvents which contains no water and is capable of dissolving the chemical adsorbate compound may be employed. Examples of such solvents include, as aprotic solvents, chlorine-based solvents such as chlorine, aromatic solvents such as benzene and toluene, lactone-based solvents such as γ-butyrolactone, ester-based solvents such as ethyl acetate, and as protic solvents, alcohol-based solvents such as methanol and ethanol.

(5) For the liquid crystal display device according to the fourth group of the invention, various types of liquid crystals may be employed, including nematic liquid crystals, smectic liquid crystals, discotic liquid crystals, and ferroelectric liquid crystals, etc. However, the liquid crystal alignment film of the present invention represented by the chemical formula 402 shows a strong alignment control effect particularly on twisted nematic (TN) type liquid crystals. Accordingly, the liquid crystal display device according to the present invention is preferable to be a 90° twisted nematic liquid crystal display device employing TN liquid crystals. Examples of the TN liquid crystals include biphenyl types, terphenyl types, azoxy type, Schiff base types, phenylcyclohexane types, biphenylcyclohexane types, ester types, pyrimidine types, dioxane types, bicyclooctane types, and cubans types.

(6) In the foregoing Examples 4-1 to 4-4, the aggregate of adsorbed molecules (thin film) was formed on the substrate by contacting the chemical adsorbate compound with the surface of the substrate already provided with an electrode. However, it is also possible that an underlayer (a layer of another substance) having hydrophilic groups is firstly provided on a surface of a substrate having an electrode, and thereafter the chemical adsorbate compound is chemically bonded to the substrate surface via the underlayer. This method is particularly effective in the case where the substrate surface has few hydrophilic groups. Examples usable as the underlayer include layers having hydrophilic groups such as OH groups, COOH groups, $NH_2$ groups, NH groups, and SH groups on their surfaces. Specifically, $SiO_2$ layer, $TiO_2$ layer, and the like may be employed.

As has been described above, the fourth group of the invention can provide a remarkably thin and uniform liquid crystal alignment film free from alignment defects, in comparison with conventional organic polymer-based liquid crystal alignment films. The liquid crystal alignment film according to the fourth group of the invention has such a structure that the adsorbed molecules are firmly bonded and fixed onto the electrode surface by chemical adsorption and the adsorbed molecules are crosslinked with each other. Therefore, the liquid crystal alignment film is excellent in durability and adherence to the substrate, and moreover, the alignment control characteristics of the film do not degrade by external factors such as heat and friction.

In addition, the liquid crystal alignment film according to the fourth group of the invention is a monomolecular thin film composed of an aggregate of the adsorbed molecules, and has an extremely small thickness. Therefore, the alignment film does not obstruct light transmission, nor disturb the electric field driving the liquid crystal since the electrical resistivity is small. Furthermore, since every individual adsorbed molecule in the alignment film controls the alignment of each of the liquid crystal molecules, the alignment film achieves remarkably good alignment control characteristics.

Further, according to producing methods of the fourth group of the invention, multi-domain type liquid crystal alignment films in which alignment directions differ in each of the domains divided in a pattern-like manner can be produced in a relatively simple manner. By employing such liquid crystal alignment films produced according to the invention, it is made possible to realize, without increasing cost, homeotropic alignment mode liquid crystal display devices of multi-domain type which can achieve wide viewing angles, high quality pictures, and high contrast ratios as well as high speed responses.

Although the present invention has been fully described by way of examples with reference to the accompanying drawings, it is to be noted the various changes and modification will be apparent to those skilled in the art. Therefore, unless such changes and modifications depart from the scope of the present invention, they should be construed as being included therein.

What is claimed is:

1. A chemical adsorbate compound for forming a thin film represented by the chemical formula 101:

Chemical Formula 101

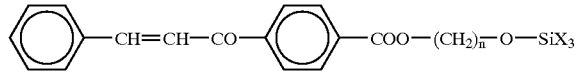

where n is an integer from 1 to 20 and X is a halogen.

2. A chemical adsorbate compound for forming a thin film according to claim 1, wherein n is an integer from 5 to 10 and X is chlorine in the chemical formula 101.

3. A method for producing a chemical adsorbate compound for forming a thin film comprising at least the steps of:

reacting benzaldehyde and 4-acetylbenzoic acid by aldol condensation to synthesize a first chalcone derivative represented by the chemical formula 102:

Chemical Formula 102

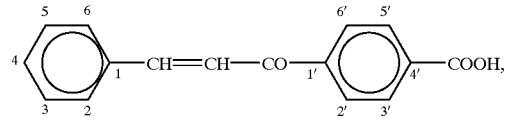

said first chalcone derivative wherein a carbonyl group is bonded at the 4' position of the benzene ring in the chalcone skeleton; and after said step of reacting benzaldehyde and 4-acetylbenzoic, reacting an alcohol derived from said first chalcone derivative with an $SiX_4$ where X is a halogen in an inert gas atmosphere by dehydrohalogenation, to synthesize a second chalcone derivative having an —O—$SiX_3$ group and a characteristic group represented by the chemical formula 103:

Chemical Formula 103

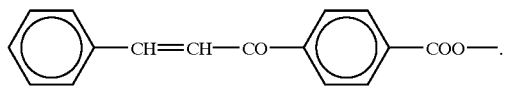

4. A method for producing a chemical adsorbate compound for forming a thin film according to claim 3, wherein said second chalcone derivative is a compound represented by the chemical formula 101:

Chemical Formula 101

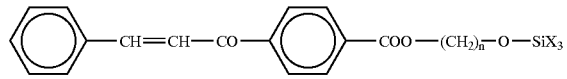

where n is an integer from 1 to 20 and X is a halogen.

5. A method for producing a chemical adsorbate compound for forming a thin film according to claim 4, wherein n is an integer from 5 to 10 and X is chlorine in the formula 101.

6. A liquid crystal alignment film comprising:

an aggregate of adsorbed molecules chemically adsorbed directly or via a layer of another substance onto a substrate having an electrode formed thereon by siloxane bonds; and each of said adsorbed molecules comprising an —O—Si bond group at an end of the molecule and a characteristic group represented by the chemical formula 201:

Chemical Formula 201

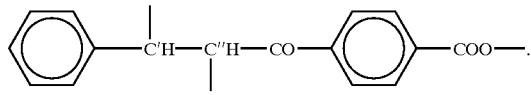

7. A liquid crystal alignment film according to claim 6, wherein said adsorbed molecules are crosslinked with each other at the carbon C' and/or the carbon C" in the chemical formula 201.

8. A liquid crystal alignment film according to claim 7, wherein said adsorbed molecules in said aggregate are aligned in a predetermined direction.

9. A liquid crystal alignment film according to claim 7, wherein said liquid crystal alignment film has a plurality of domains such that a single pixel region is divided into said plurality of domains in a pattern-like manner, and an inclination and/or alignment direction of long axes of said adsorbed molecules with respect to a substrate surface plane is/are different in said plurality of domains next to each other.

10. A liquid crystal alignment film according to claim 7, wherein a film thickness of said liquid crystal alignment film is from 0.5 nm to less than 10 nm.

11. A liquid crystal alignment film according to claim 7, wherein said liquid crystal alignment film is a monomolecular thin film.

12. A liquid crystal alignment film according to claim 6, wherein each of said adsorbed molecules is composed of a compound represented by the chemical formula 202:

Chemical Formula 202

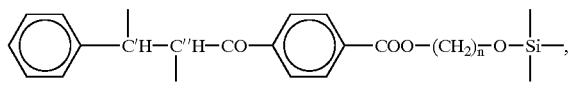

where n is an integer from 1 to 20.

13. A liquid crystal alignment film according to claim 12, wherein said adsorbed molecules are crosslinked with each other at the carbon C' and/or the carbon C" in the chemical formula 202.

14. A liquid crystal alignment film according to claim 13, wherein said adsorbed molecules in said aggregate are aligned in a predetermined direction.

15. A liquid crystal alignment film according to claim 13, wherein said liquid crystal alignment film has a plurality of domains such that a single pixel region is divided into said plurality of domains in a pattern-like manner, and an inclination and/or alignment direction of long axes of said adsorbed molecules with respect to a substrate surface plane is/are different in said plurality of domains next to each other.

16. A liquid crystal alignment film according to claim 13, wherein a film thickness of said liquid crystal alignment film is from 0.5 nm to less than 10 nm.

17. A liquid crystal alignment film according to claim 13, wherein said liquid crystal alignment film is a monomolecular thin film.

18. A method for producing a liquid crystal alignment film comprising at least the steps of:
preparing a chemisorption solution by dissolving in a non-aqueous solvent a chemical adsorbate compound having an —O—Si bond group at comprising an —O—Si bond group at a molecular end and a characteristic group represented by the chemical formula 203:

Chemical Formula 203

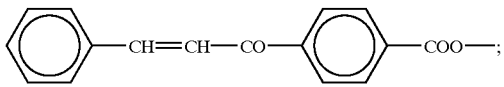

and contacting said chemisorption solution with a substrate surface having a pixel electrode formed thereon to adsorb molecules of said chemical adsorbate compound in said chemisorption solution onto said substrate surface by siloxane bonds.

19. A method for producing a liquid crystal alignment film according to claim 18, further comprising a step of drain-drying including:
after said step of contacting said chemisorption solution, rinsing said substrate surface having said adsorbed molecules thereon with a nonaqueous solvent for cleaning; and
draining and drying said solvent for cleaning remaining on said substrate surface in a predetermined direction.

20. A method for producing a liquid crystal alignment film according to claim 19, further comprising, after said step of drain-drying, irradiating said adsorbed molecules on said substrate surface with a polarized ultraviolet light so that said adsorbed molecules are crosslinked with each other at a carbon-carbon double bond shown in the chemical formula 203.

21. A method for producing a liquid crystal alignment film according to claim 20, wherein:
said steps of drain-drying and irradiating with a polarized ultraviolet light are repeated a plurality of times;
said direction of draining and drying is varied each time of said step of drain-drying; and
one of a) a region to be irradiated with said ultraviolet light and a direction of said ultraviolet light, b) a region to be irradiated with said ultraviolet light and an incident angle of said ultraviolet light, and c) a region to be irradiated with said ultraviolet light, a direction of said ultraviolet light, and an angle of applying the ultraviolet light, is varied each time of said step of irradiating,
whereby an inclination and/or alignment direction of long axes of said adsorbed molecules is/are varied in a plurality of domains such that a single pixel region is divided into said plurality of domains in a pattern-like manner.

22. A method for producing a liquid crystal alignment film according to claim 19, wherein an aprotic solvent is used for said nonaqueous solvent for cleaning in said step of rinsing, whereby unreacted chemical adsorbate compound is removed by rinsing said substrate surface to form a monomolecular thin film.

23. A method for producing a liquid crystal alignment film according to claim 19, wherein a mixed solvent of an aprotic solvent and a protic solvent is used for said nonaqueous solvent for cleaning in said step of rinsing, whereby unreacted chemical adsorbate compound is removed by rinsing said substrate surface to form a monomolecular thin film.

24. A method for producing a liquid crystal alignment film according to claim 19, wherein said chemical adsorbate compound is a compound represented by the chemical formula 204:

Chemical Formula 204

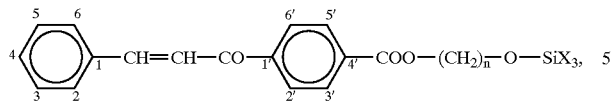

where n is an integer from 1 to 20, and X is a halogen.

25. A method for producing a liquid crystal alignment film according to claim 24, further comprising, after said step of drain-drying, irradiating said adsorbed molecules on said substrate surface with a polarized ultraviolet light so that said adsorbed molecules are crosslinked with each other at a carbon-carbon double bond shown in the chemical formula 204.

26. A method for producing a liquid crystal alignment film according to claim 25, wherein:

said steps of drain-drying and irradiating with a polarized ultraviolet light are repeated a plurality of times;

said direction of draining and drying is varied each time of said step of drain-drying; and one of a) a region to be irradiated with said ultraviolet light and a direction of said ultraviolet light, b) a region to be irradiated with said ultraviolet light and an incident angle of said ultraviolet light, and c) a region to be irradiated with said ultraviolet light, a direction of said ultraviolet light, and an angle of applying the ultraviolet light, is varied each time of said step of irradiating, whereby an inclination and/or alignment direction of long axes of said adsorbed molecules is/are varied in a plurality of domains such that a single pixel region is divided into said plurality of domains in a pattern-like manner.

27. A method for producing a liquid crystal alignment film according to claim 24, wherein an aprotic solvent is used for said nonaqueous solvent fbr cleaning in said step of rinsing, whereby unreacted chemical adsorbate compound is removed by rinsing said substrate surface to form a monomolecular thin film.

28. A method for producing a liquid crystal alignment film according to claim 24, wherein a mixed solvent of an aprotic solvent and a protic solvent is used for said nonaqueous solvent for cleaning in said step of rinsing, whereby unreacted chemical adsorbate compound is removed by rinsing said substrate surface to form a monomolecular thin film.

29. A liquid crystal display device comprising:

a pair of opposed substrates, a liquid crystal alignment film provided on a surface of at least one of said substrates, said surface having an electrode thereon, and a liquid crystal enclosed in a cell gap between said pair of substrates, said liquid crystal display device wherein:

said liquid crystal alignment film comprises an aggregate of adsorbed molecules chemically adsorbed directly or via a layer of another substance onto said surface of said substrate having said electrode thereon by siloxane bonds, and each of said adsorbed molecules comprises an —O—Si bond group at an end of the molecule and a characteristic group represented by the chemical formula 201:

Chemical Formula 201

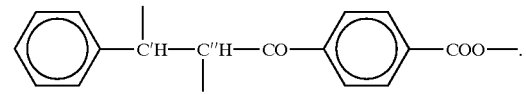

30. A liquid crystal display device according to claim 29, wherein said adsorbed molecules are crosslinked with each other at the carbon C' and/or the carbon C" in the chemical formula 201.

31. A liquid crystal display device according to claim 30, wherein each of said adsorbed molecules is composed of a compound represented by the chemical formula 202:

Chemical Formula 202

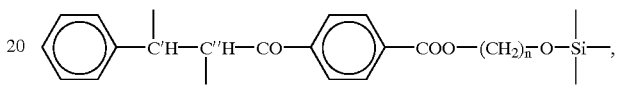

where n is an integer from 1 to 20.

32. A liquid crystal display device according to claim 31, wherein a film thickness of said liquid crystal alignment film is from 0.5 nm to less than 10 nm.

33. A liquid crystal display device according to claim 31, wherein said liquid crystal alignment film is a monomolecular thin film.

34. A liquid crystal display device according to claim 31, wherein a pretilt angle, a pretilt orientation, or both of liquid crystal molecules in said cell gap is/are controlled by an inclination direction, an alignment direction, or both of long axes of adsorbed molecules with respect to a substrate surface plane.

35. A liquid crystal display device according to claim 31, wherein said liquid crystal alignment film has a plurality of domains such that a single pixel region is divided into said plurality of domains in a pattern-like manner, and an inclination and/or alignment direction of long axes of said adsorbed molecules with respect to a substrate surface plane is/are different in said plurality of domains next to each other.

36. An in-plane type liquid crystal display device comprising:

a substrate, a pixel electrode provided on said substrate, a counter electrode also provided on said substrate on which said pixel electrode is provided, and a liquid crystal alignment film formed on a surface of said substrates on which both of said electrodes are provided;

said liquid crystal display device wherein:

said liquid crystal alignment film comprises an aggregate of adsorbed molecules chemically adsorbed directly or via a layer of another substance onto said surface of said substrate having said electrode thereon by siloxane bonds, and each of said adsorbed molecules comprises an —O—Si bond group at an end of the molecule and a characteristic group represented by the chemical formula 201:

Chemical Formula 201

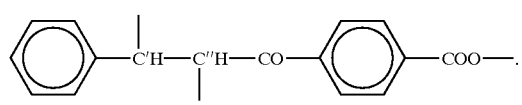

37. A liquid crystal display device according to claim 36, wherein said adsorbed molecules are crosslinked with each other at the carbon C' and /or the carbon C" in the chemical formula 201.

38. A liquid crystal display device according to claim 37, wherein each of said adsorbed molecules is composed of a compound represented by the chemical formula 202:

Chemical Formula 202

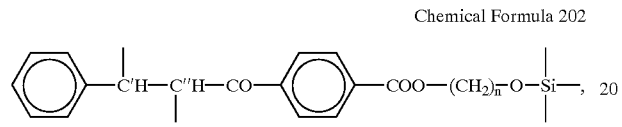

where n is an integer from 1 to 20.

39. A liquid crystal display device according to claim 38, wherein a film thickness of said liquid crystal alignment film is from 0.5 nm to less than 10 nm.

40. A liquid crystal display device according to claim 38, wherein said liquid crystal alignment film is a monomolecular thin film.

41. A liquid crystal display device according to claim 38, wherein a pretilt angle, a pretilt orientation, or both of liquid crystal molecules in said cell gap is/are controlled by an inclination direction, an alignment direction, or both of long axes of said adsorbed molecules with respect to a substrate surface plane.

42. A liquid crystal display device according to claim 38, wherein said liquid crystal alignment film has a plurality of domains such that a single pixel region is divided into said plurality of domains in a pattern-like manner, and an inclination and/or alignment direction of long axes of said adsorbed molecules with respect to a substrate surface plane is/are different in said plurality of domains next to each other.

43. A chemical adsorbate compound for forming a thin film represented by the chemical formula 301:

Chemical Formula 301

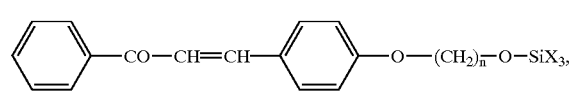

where n is an integer from 1 to 20 and X is a halogen.

44. A chemical adsorbate compound for forming a thin film according to claim 43, wherein n is an integer from 5 to 10 and X is chlorine in the chemical formula 301.

45. A method for producing a chemical adsorbate compound for forming a thin film comprising at least the steps of:

reacting 4-hydroxybenzaldehyde and acetophenone by aldol condensation to synthesize a first compound having an hydroxyl group at the 4 position of the benzene ring in the chalcone skeleton, said first compound represented by the chemical formula 302:

Chemical Formula 302

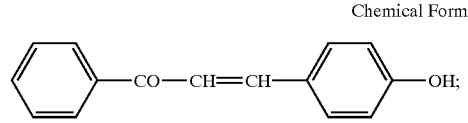

and after said step of reacting 4-hydroxybenzaldehyde and acetophenone, reacting an alcohol derived from said first compound with an $SiX_4$ where X is a halogen in an inert gas atmosphere by dehydrohalogenation, to synthesize a second compound having at least an —O—$SiX_3$ group and a characteristic group represented by the chemical formula 303:

Chemical Formula 303

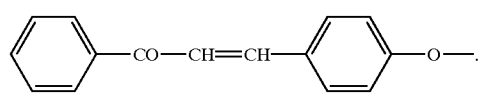

46. A method for producing a chemical adsorbate compound for forming a thin film according to claim 45, wherein said second compound is represented by the chemical formula 301:

Chemical Formula 301

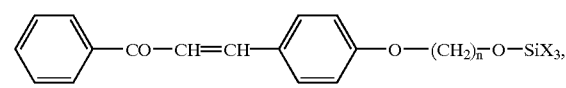

where n is an integer from 1 to 20 and X is a halogen.

47. A method of producing a chemical adsorbate compound for forming a thin film according to claim 46, wherein n is an integer from 5 to 10 in the chemical formula 301.

48. A liquid crystal alignment film comprising:

an aggregate of adsorbed molecules chemically adsorbed directly or via a layer of another substance onto a substrate having an electrode formed thereon; and each of said adsorbed molecules comprising an Si bond group at an end of the molecule and a characteristic group represented by the chemical formula 401:

Chemical Formula 401

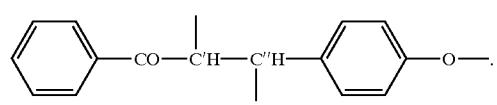

49. A liquid crystal alignment film according to claim 48, wherein each of said adsorbed molecules is composed of a compound represented by the chemical formula 402:

Chemical Formula 402

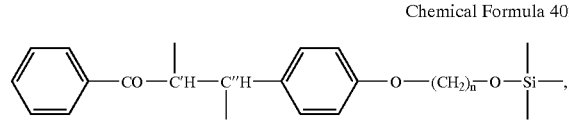

where n is an integer from 1 to 20.

50. A liquid crystal alignment film according to claim 49, wherein said adsorbed molecules in said aggregate are aligned in a predetermined direction.

51. A liquid crystal alignment film according to claim 50, wherein said adsorbed molecules are crosslinked with each other at the carbon C' and/or the carbon C" in the chemical formula 402.

52. A liquid crystal alignment film according to claim 51, wherein a film thickness of said liquid crystal alignment film is from 0.5 nm to less than 10 nm.

53. A liquid crystal alignment film according to claim 51, wherein said liquid crystal alignment film is a monomolecular thin film.

54. A liquid crystal alignment film according to claim 49, wherein said liquid crystal alignment film has a plurality of domains such that a single pixel region is divided into said plurality of domains in a pattern-like manner, and an inclination and/or alignment direction of long axes of said adsorbed molecules with respect to a substrate surface plane is/are different in said plurality of domains next to each other.

55. A liquid crystal alignment film according to claim 54, wherein said adsorbed molecules are crosslinked with each other at the carbon C' and/or the carbon C" in the chemical formula 402.

56. A liquid crystal alignment film according to claim 55, wherein a film thickness of said liquid crystal alignment film is from 0.5 nm to less than 10 nm.

57. A liquid crystal alignment film according to claim 55, wherein said liquid crystal alignment film is a monomolecular thin film.

58. A method for producing a liquid crystal alignment film comprising at least the steps of:

preparing a chemisorption solution by dissolving in a non-aqueous solvent a chemical adsorbate compound represented by the chemical formula 403:

Chemical Formula 403

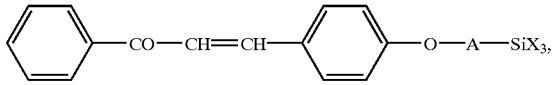

where A is a divalent functional group and X is a halogen; and contacting said chemisorption solution with a substrate surface having a pixel electrode formed thereon to adsorb molecules of said chemical adsorbate compound in said chemisorption solution onto said substrate surface.

59. A method for producing a liquid crystal alignment film according to claim 58, further comprising a step of drain-drying including:

after said step of contacting said chemisorption solution, rinsing said substrate surface having said adsorbed molecules thereon with a nonaqueous solvent for cleaning; and draining and drying said solvent for cleaning remaining on said substrate surface in a predetermined direction.

60. A method for producing a liquid crystal alignment film according to claim 59, wherein A in the chemical formula 403 is $(CH_2)_n$—O—, where n is an integer from 1 to 20.

61. A method for producing a liquid crystal alignment film according to claim 58, wherein, in the chemical formula 403, A is $(CH_2)_n$—O—, where n is an integer from 1 to 20, and X is chlorine.

62. A method for producing a liquid crystal alignment film according to claim 61, further comprising, after said step of drain-drying, irradiating said adsorbed molecules on said substrate surface with a polarized ultraviolet light so that said adsorbed molecules are crosslinked with each other at a carbon-carbon double bond shown in the chemical formula 403.

63. A method for producing a liquid crystal alignment film according to claim 62, wherein:

said steps of drain-drying and irradiating with a polarized ultraviolet light are repeated a plurality of times;

said direction of draining and drying is varied each time of said step of drain-drying; and one of a) a region to be irradiated with said ultraviolet light and a direction of said ultraviolet light, b) a region to be irradiated with said ultraviolet light and an incident angle of said ultraviolet light, and c) a region to be irradiated with said ultraviolet light, a direction of said ultraviolet light, and an angle of applying the ultraviolet light, is varied each time of said step of irradiating, whereby an inclination and/or alignment direction of long axes of said adsorbed molecules is/are varied in a plurality of domains such that a single pixel region is divided into said plurality of domains in a pattern-like manner.

64. A method for producing a liquid crystal alignment film according to claim 61, wherein an aprotic solvent is used for said nonaqueous solvent for cleaning in said step of rinsing, whereby unreacted chemical adsorbate compound is removed by rinsing said substrate surface to form a monomolecular thin film.

65. A method for producing a liquid crystal alignment film according to claim 61, wherein a mixed solvent of an aprotic solvent and a protic solvent is used for said nonaqueous solvent for cleaning in said step of rinsing, whereby unreacted chemical adsorbate compound is removed by rinsing said substrate surface to form a monomolecular thin film.

66. A liquid crystal display device comprising:

a pair of opposed substrates, a liquid crystal alignment film provided on a surface of at least one of said substrates, said surface having an electrode thereon, and a liquid crystal enclosed in a cell gap between said pair of substrates, said liquid crystal display device wherein:

said liquid crystal alignment film comprises an aggregate of adsorbed molecules chemically adsorbed directly or via a layer of another substance onto said surface of said substrate having said electrode thereon, and each of said adsorbed molecules comprises an Si bond group at an end of the molecule and a characteristic group represented by the chemical formula 401:

Chemical Formula 401

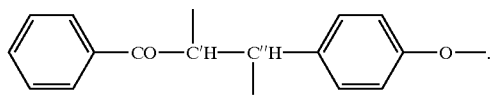

67. A liquid crystal display device according to claim 66, wherein said adsorbed molecules are crosslinked with each other at the carbon C' and/or the carbon C" in the chemical formula 401.

68. A liquid crystal display device according to claim 67, wherein each of said adsorbed molecules is composed of a compound represented by the chemical formula 402:

Chemical Formula 402

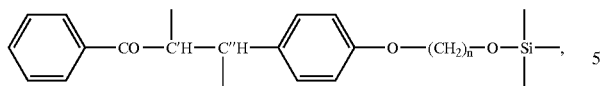

where n is an integer from 1 to 20.

69. A liquid crystal display device according to claim 68, wherein a pretilt angle, a pretilt orientation, or both of liquid crystal molecules in said cell gap is/are controlled by an inclination direction, an alignment direction, or both of long axes of said adsorbed molecules with respect to a substrate surface plane.

70. A liquid crystal display device according to claim 69, wherein a film thickness of said liquid crystal alignment film is from 0.5 am to less than 10 nm.

71. A liquid crystal display device according to claim 69, wherein said liquid crystal alignment film is a monomolecular thin film.

72. A liquid crystal display device according to claim 68, wherein said liquid crystal alignment film has a plurality of domains such that a single pixel region is divided into said plurality of domains in a pattern-like manner, and an inclination and/or alignment direction of long axes of said adsorbed molecules with respect to a substrate surface plane is/are different in said plurality of domains next to each other.

73. A liquid crystal display device according to claim 72, wherein a film thickness of said liquid crystal alignment film is from 0.5 am to less than 10 nm.

74. A liquid crystal display device according to claim 72, wherein said liquid crystal alignment film is a monomolecular thin film.

75. An in-plane switching type liquid crystal display device comprising:
a substrate, a pixel electrode provided on said substrate, a counter electrode also provided on said substrate on which said pixel electrode is provided, and a liquid crystal alignment film formed on a surface of said substrates on which both of said electrodes are provided;
said liquid crystal display device wherein:
said liquid crystal alignment film comprises an aggregate of adsorbed molecules chemically adsorbed directly or via a layer of another substance onto said surface of said substrate having said electrodes thereon, and each of said adsorbed molecules comprises an Si bond group at an end of the molecule and a characteristic group represented by the chemical formula 401:

Chemical Formula 401

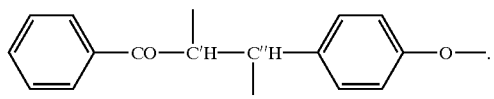

76. A liquid crystal display device according to claim 75, wherein said adsorbed molecules are crosslinked with each other at the carbon C' and/or the carbon C" in the chemical formula 401.

77. A liquid crystal display device according to claim 76, wherein each of said adsorbed molecules is composed of a compound represented by the chemical formula 402:

Chemical Formula 402

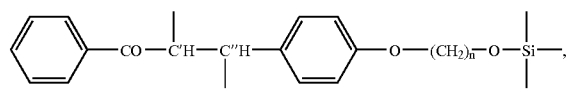

where n is an integer from 1 to 20.

78. A liquid crystal display device according to claim 77, wherein a pretilt angle, a pretilt orientation, or both of liquid crystal molecules in said cell gap is/are controlled by an inclination direction, an alignment direction, or both of long axes of said adsorbed molecules with respect to a substrate surface plane.

79. A liquid crystal display device according to claim 78, wherein a film thickness of said liquid crystal alignment film is from 0.5 nm to less than 10 nm.

80. A liquid crystal display device according to claim 78, wherein said liquid crystal alignment film is a monomolecular thin film.

81. A liquid crystal display device according to claim 77, wherein said liquid crystal alignment film has a plurality of domains such that a single pixel region is divided into said plurality of domains in a pattern-like manner, and an inclination and/or alignment direction of long axes of said adsorbed molecules with respect to a substrate surface plane is/are different in said plurality of domains next to each other.

82. A liquid crystal display device according to claim 81, wherein a film thickness of said liquid crystal alignment film is from 0.5 nm to less than 10 nm.

83. A liquid crystal display device according to claim 81, wherein said liquid crystal alignment film is a monomolecular thin film.

* * * * *

UNITED STATES PATENT AND TRADEMARK OFFICE
CERTIFICATE OF CORRECTION

PATENT NO. : 6,451,392 B1
DATED : September 17, 2002
INVENTOR(S) : Tadashi Ootake et al.

It is certified that error appears in the above-identified patent and that said Letters Patent is hereby corrected as shown below:

Column 47,
Line 41, change "fbr" to -- for --.

Signed and Sealed this

Eighteenth Day of March, 2003

JAMES E. ROGAN
*Director of the United States Patent and Trademark Office*